(12) United States Patent
Luo et al.

(10) Patent No.: US 12,358,855 B2
(45) Date of Patent: *Jul. 15, 2025

(54) CATALYTIC CRACKING AGENT CONTAINING PHOSPHORUS-MODIFIED MOLECULAR SIEVE, PREPARATION PROCESS THEREOF, PREPARATION SYSTEM AND USE THEREOF

(71) Applicants: CHINA PETROLEUM & CHEMICAL CORPORATION, Beijing (CN); SINOPEC RESEARCH INSTITUTE OF PETROLEUM PROCESSING CO., LTD., Beijing (CN)

(72) Inventors: Yibin Luo, Beijing (CN); Chengqiang Wang, Beijing (CN); Ying Ouyang, Beijing (CN); Enhui Xing, Beijing (CN); Xingtian Shu, Beijing (CN)

(73) Assignees: CHINA PETROLEUM & CHEMICAL CORPORATION, Beijing (CN); SINOPEC RESEARCH INSTITUTE OF PETROLEUM PROCESSING CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/260,971

(22) PCT Filed: Jan. 11, 2022

(86) PCT No.: PCT/CN2022/071280
§ 371 (c)(1),
(2) Date: Jul. 11, 2023

(87) PCT Pub. No.: WO2022/148471
PCT Pub. Date: Jul. 14, 2022

(65) Prior Publication Data
US 2024/0059630 A1    Feb. 22, 2024

(30) Foreign Application Priority Data

Jan. 11, 2021 (CN) .................. 202110028578.8
Jan. 11, 2021 (CN) .................. 202110030461.3

(51) Int. Cl.
*B01J 29/82* (2006.01)
*B01J 21/16* (2006.01)
(Continued)

(52) U.S. Cl.
CPC .................. *C07C 4/06* (2013.01); *B01J 21/16* (2013.01); *B01J 29/084* (2013.01); *B01J 29/40* (2013.01);
(Continued)

(58) Field of Classification Search
CPC ......... C07C 4/06; C07C 4/10; C07C 2529/08; C07C 2529/40; B01J 21/04; B01J 21/16;
(Continued)

(56) References Cited

U.S. PATENT DOCUMENTS 3,758,403 A   9/1973   Rosinski et al.
5,171,921 A   12/1992  Gaffney et al.
(Continued)

FOREIGN PATENT DOCUMENTS

CN    1506161 A      6/2004
CN    106994364 A    8/2017
(Continued)

OTHER PUBLICATIONS

Ding, Jian et al., "Combined desilication and phosphorus modification for high-silica ZSM-5 zeolite with related study of hydrocarbon cracking performance", Applied Catalysis A: General, Aug. 25, 2015, vol. 503, pp. 147-155.

*Primary Examiner* — Bobby Ramdhanie
*Assistant Examiner* — Jason Y Chong
(74) *Attorney, Agent, or Firm* — NKL Law; Allen Xue

(57) ABSTRACT

A catalytic cracking agent has an active component consisting of a phosphorus-modified molecular sieve and a non-
(Continued)

phosphorus-modified molecular sieve or only consisting of a phosphorus-modified molecular sieve. According to an electron probe microanalysis (EPMA), the D value of phosphorus in the catalytic cracking agent is ≥65%, preferably ≥68%, provided that the active component consists of the phosphorus-modified molecular sieve and the non-phosphorus-modified molecular sieve, or the D value of phosphorus in the catalytic cracking agent is ≥82%, preferably ≥84%, provided that the active component only consists of the phosphorus-modified molecular sieve.

19 Claims, 4 Drawing Sheets

(51) Int. Cl.
| | |
|---|---|
| *B01J 29/08* | (2006.01) |
| *B01J 29/40* | (2006.01) |
| *B01J 29/80* | (2006.01) |
| *B01J 37/00* | (2006.01) |
| *B01J 37/10* | (2006.01) |
| *B01J 37/28* | (2006.01) |
| *C07C 4/06* | (2006.01) |

(52) U.S. Cl.
CPC ........... *B01J 29/80* (2013.01); *B01J 37/0018* (2013.01); *B01J 37/10* (2013.01); *B01J 37/28* (2013.01); *B01J 2229/16* (2013.01); *B01J 2229/183* (2013.01); *B01J 2229/24* (2013.01); *C07C 2529/08* (2013.01); *C07C 2529/40* (2013.01)

(58) Field of Classification Search
CPC . B01J 29/08; B01J 29/084; B01J 29/40; B01J 29/80; B01J 29/82; B01J 29/85; B01J 37/0018; B01J 37/0201; B01J 37/10; B01J 37/28; B01J 2229/16; B01J 2229/183; B01J 2229/186; B01J 2229/24; B01J 2229/37; B01J 27/14; B01J 27/16; Y02P 20/52; C01B 39/10; C01B 39/38
See application file for complete search history.

(56) References Cited

U.S. PATENT DOCUMENTS

| | | |
|---|---|---|
| 5,997,728 A | 12/1999 | Adewuyi et al. |
| 2014/0018232 A1 | 1/2014 | Wang et al. |
| 2014/0194662 A1 | 7/2014 | Nesterenko et al. |
| 2023/0202851 A1* | 6/2023 | Luo ..................... C01B 39/026 502/77 |

FOREIGN PATENT DOCUMENTS

| | | |
|---|---|---|
| CN | 112138710 A | 12/2020 |
| CN | 113526519 A | 10/2021 |
| CN | 113526520 A | 10/2021 |
| EA | 30477 B1 | 8/2018 |
| RU | 2310506 C2 | 11/2007 |
| RU | 2634702 C2 | 11/2017 |
| RU | 2709521 C1 | 12/2019 |

* cited by examiner

US 12,358,855 B2

CATALYTIC CRACKING AGENT CONTAINING PHOSPHORUS-MODIFIED MOLECULAR SIEVE, PREPARATION PROCESS THEREOF, PREPARATION SYSTEM AND USE THEREOF

TECHNICAL FIELD

The present invention relates to a catalytic cracking agent containing a phosphorus-modified molecular sieve, a preparation process and preparation system thereof, and use thereof. More particularly, the present invention relates to a catalytic cracking catalyst containing a phosphorus-modified MFI-structured molecular sieve or a catalytic cracking auxiliary containing a phosphorus-modified MFI-structured molecular sieve, a short-stage preparation process and preparation system thereof, and use thereof.

BACKGROUND TECHNOLOGY

ZSM-5 molecular sieve/zeolite having an MFI structure is a widely used zeolite/molecular sieve catalytic material developed by Mobil Corporation of the United States in 1972. ZSM-5 molecular sieve has a structure of three-dimensional intersectional channels. The channels along the a-axis are straight channels having a sectional dimension of 0.54×0.56 nm and being approximately circular. The channels along the b-axis are zigzag channels having a sectional dimension of 0.51×0.56 nm and being elliptical. ZSM-5 molecular sieve has openings composed of ten-membered rings, and are between the small-pore zeolite and the large-pore zeolite in the size of the openings, so it has a unique shape-selective catalytic effect. ZSM-5 molecular sieve has a unique pore-channel structure, a good shape-selective catalysis and isomerization performance, a high thermal and hydrothermal stability, a high specific surface area, a wide silica-alumina ratio variation range, a unique surface acidity and a relatively low carbon formation. It is widely used as catalyst and catalyst support, and has been successfully used in production processes such as alkylation, isomerization, disproportionation, catalytic cracking, methanol-to-gasoline, and methanol-to-olefins. ZSM-5 molecular sieve is introduced into catalytic cracking and C4 hydrocarbon catalytic cracking and shows excellent catalytic performance, and the utilization of its molecular shape selectivity can greatly improve the yield of light olefins.

Since 1983, ZSM-5 molecular sieve has been used as a catalytic cracking octane promotion catalyst in the catalytic cracking process, aiming to improve the octane number of catalytic cracking gasoline and the selectivity of lower carbon olefins. U.S. Pat. No. 3,758,403 first reported the preparation of FCC catalysts by using ZSM-5 as an active component for increasing the propylene production together with REY. U.S. Pat. No. 5,997,728 disclosed the use of an unmodified ZSM-5 molecular sieve as auxiliary for increasing the propylene production. However, their propylene yields were not high. Although ZSM-5 molecular sieve has good shape selectivity performance and isomerization performance, its disadvantage is poor hydrothermal stability, and it is easy to deactivate under a rigorous high-temperature hydrothermal condition, which reduces the catalytic performance.

In the 1980s, Mobil Corporation discovered that phosphorus can improve the hydrothermal stability of ZSM-5 molecular sieve, and at the same time, the modification of ZSM-5 molecular sieve with phosphorus can increase the yield of lower carbon olefins. Conventional additives usually contain phosphorus-activated ZSM-5, which selectively converts primary cracked products (e.g., gasoline olefins) to C3 and C4 olefins. ZSM-5 molecular sieve is modified by introducing an appropriate amount of inorganic phosphorus compounds after synthesis, which can stabilize the framework aluminum under a rigorous hydrothermal condition.

CN106994364A discloses a process for a phosphorus-modified ZSM-5 molecular sieve. The process comprises firstly mixing one or more phosphorus-containing compounds selected from phosphoric acid, diammonium hydrogen phosphate, ammonium dihydrogen phosphate and ammonium phosphate with a ZSM-5 molecular sieve having high alkali metal ion content to obtain a mixture with a phosphorus loading (as $P_2O_5$) of at least 0.1 wt %, drying and calcining the mixture, then performing an ammonium-exchanging step and a water-washing step so that the alkali metal ion content is reduced to 0.10 wt % or less, and then performing steps of drying and hydrothermal aging at 400-1000° C. under 100% water vapor. The phosphorus-containing ZSM-5 molecular sieve obtained by this process has high total acid content, excellent cracking conversion rate and propylene selectivity, and relatively high liquefied gas yield.

CN1506161A discloses a process for modifying a hierarchical ZSM-5 molecular sieve. This process comprises producing a hierarchical ZSM-5 molecular sieve according to the conventional steps: synthesis→filtering→ammonium exchanging→drying→calcining, and then modifying the hierarchical ZSM-5 molecular sieve with phosphoric acid, drying and calcining to obtain a phosphorus-modified hierarchical ZSM-5 molecular sieve, wherein the $P_2O_5$ loading is usually in the range of 1-7 wt %. However, phosphoric acid or phosphoric acid ammonium salts will self-aggregate to form phosphorus species in different aggregation states during the calcining process. During the hydrothermal treatment process, only the phosphate groups entering the pores interact with the framework aluminum to retain the B acid center, reducing the distribution of phosphorus species.

Although the modification of a ZSM-5 molecular sieve with an appropriate amount of an inorganic phosphorus compound can retard the framework dealumination and improve the hydrothermal stability, and phosphorus atoms will combine with the distorted four-coordinated framework aluminum to form weak B acid centers, so as to achieve higher conversion of long-chain alkane cracking and higher light olefin selectivity, but the modification of a ZSM-5 molecular sieve with an excessive inorganic phosphorus compound will block the pore channels of the molecular sieve, reduces the pore volume and the specific surface area, and occupies a large amount of strong B acid centers. Moreover, in the prior art, phosphoric acid or phosphoric acid ammonium salts will self-polymerize to form phosphorus species in different aggregation states during the calcining process, the coordination of phosphorus and the framework aluminum is insufficient, the utilization efficiency of phosphorus is relatively low, and the phosphorus modification does not always achieve satisfactory hydrothermal stability improvement results. Therefore, new technologies are urgently needed to promote the coordination of phosphorus and the framework aluminum, improve the hydrothermal stability of the phosphorus-modified ZSM-5 molecular sieve, and further increase the cracking activity. Catalytic cracking catalyst and catalytic cracking auxiliary, both of them are collectively referred to as catalytic cracking agent herein. The difference between them lies in that the active components are different, generally, the catalytic cracking agent containing only the phosphorus-modified molecular sieve is referred to as the catalytic cracking auxiliary, and the catalytic cracking agent containing a phosphorus-modified molecular sieve and at least one non-phosphorus-modified molecular sieve (i.e, a molecular sieve that is not modified with phosphorus) is referred to as the catalytic cracking catalyst. In the prior art industrial production, the preparation processes of catalytic cracking catalysts or catalytic cracking auxiliaries are similar (see FIGS. 1 and 2), including the phosphorus-modification (the impregnation treatment with a phosphorus-containing solution) of the MFI-structured molecular sieve, the drying (flash drying), and the first calcining, the mixing and shaping of raw materials (including the phosphorus-modified MFI-structured molecular sieve and other molecular sieves (if any), inorganic binders, etc.), and the second calcining to produce the finished products of catalytic cracking catalysts or catalytic cracking auxiliaries. In order to improve the hydrothermal stability of phosphorus exchange-modified MFI-structured molecular sieves, the existing technology requires two calcining processes, therefore the preparation cost is high and the preparation process is relatively complicated.

SUMMARY OF THE INVENTION

Aiming at the problems of the prior art, i.e., the complicated phosphorus-modification process caused by the improvement of the hydrothermal stability of the molecular sieves such as the MFI-structured molecular sieve in catalytic cracking catalysts or catalytic cracking auxiliaries, and the relatively complex preparation process of catalytic cracking catalysts or catalytic cracking auxiliaries, one of the objects of the present invention is to provide a simplified preparation process of the catalytic cracking catalyst or the catalytic cracking auxiliary, and thereby the obtained catalytic cracking catalyst or catalytic cracking auxiliary (in the present invention, collectively referred to as catalytic cracking agent). The second object of the present invention is to provide a preparation system for the preparation process for the above-mentioned simplified process.

In order to achieve the above objects, the present invention provides a process for preparing a catalytic cracking agent (catalytic cracking catalyst or catalytic cracking auxiliary), which is characterized in that the process comprises:
(1) mixing the following components as raw material and slurrying the raw material, and shaping into shaped bodies:
a phosphorus-modified molecular sieve (e.g. a phosphorus-modified MF-structured molecular sieve); optionally, a non-phosphorus-modified molecular sieve (e.g., an FAU-structured molecular sieve such as a Y-type molecular sieve);
an inorganic binder; and
optionally, a second clay;
(2) a hydrothermal calcining treatment is performed on the shaped bodies under an atmosphere condition in which an external pressure is applied and an aqueous solution is externally added; said phosphorus-modified molecular sieve is obtained through impregnation-contacting (exchanging) a molecular sieve having a temperature of 0-150° C. with an aqueous solution of a phosphorus-containing compound having a temperature of 0-150° C.;
said hydrothermal calcining treatment is performed at a temperature of 200-800° C. under a gauge pressure of 0.01-1.0 MPa in an atmosphere containing 1-100% water vapor.

In order to achieve the above objects, the present invention further provides an agent, the active component of which consists of a phosphorus-modified molecular sieve (e.g. a phosphorus-modified MFI-structured molecular sieve) and a non-phosphorus-modified molecular sieve (for example a FAU-structured molecular sieve, such as a Y-type molecular sieve), or only consists of a phosphorus-modified molecular sieve (e.g. a phosphorus-modified MFI-structured molecular sieve), with the electron probe microanalysis (EPMA),
the D value of phosphorus in the catalytic cracking agent is ≥65%, preferably ≥68%, provided that the active component consists of a phosphorus-modified molecular sieve (e.g. a phosphorus-modified MFI-structured molecular sieve) and a non-phosphorus-modified molecular sieve (for example a FAU-structured molecular sieve, such as a Y-type molecular sieve), or
the D value of phosphorus in the catalytic cracking agent is ≥82%, preferably ≥84%, provided that the active component only consists of a phosphorus-modified molecular sieve (e.g. a phosphorus-modified MFI-structured molecular sieve).

In the present invention, on the dry basis, the catalytic cracking agent or the catalytic cracking catalyst contain:
1-25 wt % of a non-phosphorus-modified molecular sieve (e.g., an FAU-structured molecular sieve, such as a Y-type molecular sieve);
5-50 wt % of a phosphorus-modified molecular sieve (e.g. a phosphorus-modified MFI-structured molecular sieve);
1-60 wt % of an inorganic binder; and
optionally, 0-60 wt % of a second clay.

In the present invention, on the dry basis, the catalytic cracking agent or the catalytic cracking auxiliary contains:
5-75 wt % of a phosphorus-modified molecular sieve (e.g. a phosphorus-modified MFI-structured molecular sieve), free of a non-phosphorus-modified molecular sieve;
1-40 wt % of an inorganic binder; and
optionally, 0-65 wt % of a second clay.

In the present invention, the non-phosphorus-modified molecular sieve (e.g., an FAU-structured molecular sieve, such as a Y-type molecular sieve) comprises at least one of a PSRY molecular sieve, a rare earth-containing PSRY molecular sieve, an USY molecular sieve, a rare earth-containing USY molecular sieve, a REY molecular sieve, a REHY molecular sieve and an HY molecular sieve.

In the present invention, the inorganic binder comprises at least one of pseudo-boehmite, alumina sol, silica-alumina sol, water glass and phosphorus-aluminum inorganic binder; preferably, the inorganic binder contains a phosphorus-aluminum inorganic binder, more preferably, the inorganic binder is a phosphorus-aluminum inorganic binder. The phosphorus-aluminum inorganic binder is a phosphorus aluminate binder and/or a first clay-containing phosphorus-aluminum inorganic binder. In case that the phosphorus-aluminum inorganic binder is a phosphorus aluminate binder and/or a first clay-containing phosphorus-aluminum inorganic binder, the first clay-containing phosphorus-aluminum inorganic binder is based on the dry basis, the first clay-containing phosphorus-aluminum inorganic binder contains 15-40 wt % of an aluminum component (as $Al_2O_3$), 45-80 wt % of a phosphorus component (as $P_2O_5$) and greater than 0 and not more than 40 wt % of a first clay, and the first clay-containing phosphorus-aluminum inorganic binder has a P/Al weight ratio of 1.0-6.0, a pH of 1-3.5, and a solid content of 15-60 wt %; the first clay comprises at least one of kaolin, sepiolite, attapulgite, rectorite, montmorillonite and diatomite. The second clay is selected from at least one of kaolin, sepiolite, attapulgite, rectorite, montmorillonite, glagerite, halloysite, hydrotalcite, bentonite and diatomite.

In the preparation process of the present invention, the phosphorus-containing compound used in the phosphorus modification can be selected from organic phosphorus compounds and/or inorganic phosphorus compounds. The organic phosphorus compound for example can be selected from trimethyl phosphate, triphenylphosphine, trimethyl phosphite, tetrabutylphosphonium bromide, tetrabutylphosphonium chloride, tetrabutylphosphonium hydroxide, triphenylethylphosphonium bromide, triphenylbutylphosphonium bromide, triphenylbenzylphosphonium bromide, hexamethylphosphoric triamide, dibenzyl diethylphosphoramidite, and 1, 3-bis((triethyl-phosphaneyl)methyl) benzene; and the inorganic phosphorus compound for example can be selected from phosphoric acid, ammonium hydrogen phosphate, diammonium hydrogen phosphate, ammonium phosphate, and boron phosphate.

In the preparation process of the present invention, in said molecular sieve to be phosphorus-modified, $Na_2O<0.1$ wt %. Said molecular sieve to be phosphorus-modified is a micropore ZSM-5 molecular sieve or a hierarchical ZSM-5 molecular sieve. The micropore ZSM-5 molecular sieve has a silica/alumina molar ratio of 15-1000, preferably 20-200. The hierarchical ZSM-5 molecular sieve has a proportion of the mesopore volume relative to the total pore volume of greater than 10%, an average pore size of 2-20 nm, and a silica/alumina molar ratio of 15-1000, preferably 20-200. In the preparation process of the present invention, when the molecular sieve to be phosphorus-modified is impregnation-exchanged with an aqueous solution of a phosphorus-containing compound, the molar ratio of the phosphorus-containing compound (as phosphorus) to the molecular sieve to be phosphorus-modified (as aluminum) is 0.01-2; preferably, 0.1-1.5; more preferably, 0.2-1.5. Upon impregnation-exchanging, the weight ratio of water/molecular sieve is 0.5-1. Since said impregnation-exchanging at a higher temperature can produce a better result, i.e., the better dispersion of phosphorus species, and the easier migration of phosphorus into the intracrystalline porosity of the molecular sieve and combine with the framework aluminum during the subsequent pressurized calcination of the catalyst raw material, which further improves the coordination degree of phosphorus and the framework aluminum, and finally contributes to improving the hydrothermal stability of the molecular sieve. Therefore, said impregnation-exchanging is preferably performed at a higher temperature, preferably 50-150° C., more preferably 70-130° C. for 0.5-40 hours.

In the preparation process of the present invention, the atmosphere condition has a gauge pressure of 0.01-1.0 MPa, for example 0.1-0.8 MPa, preferably 0.3-0.6 MPa and contains 1%-100% water vapor, for example, 30%-100% water vapor, preferably 60-100% water vapor; said hydrothermal calcining treatment is performed at 200-800° C., preferably 300-500° C. The externally applied pressure refers to applying a certain pressure from the outside during the process of hydrothermally calcining the auxiliary raw material. For example, it can be carried out by introducing an inert gas from the outside to maintain a certain backpressure. The amount of externally added water is to meet the requirement that the atmosphere condition contains 1-100% water vapor.

In the present invention, for example, to contain 1-100% water vapor refers to an air atmosphere having a moisture content of at least 1% or 100% water vapor atmosphere (pure water vapor atmosphere).

In the present invention, based on the total amount of the catalytic cracking catalyst or the catalytic cracking auxiliary, a specific embodiment for the composition of the inorganic binder comprises 3-39 wt % of the phosphorus-aluminum inorganic binder on the dry basis and 1-30 wt % of other inorganic binder(s) on the dry basis, wherein the other inorganic binder comprises pseudo-boehmite, alumina sol, silica-alumina sol and water glass.

In the preparation process of the present invention, preferably, the first clay-containing phosphorus-aluminum inorganic binder is prepared with the following steps: an alumina source, a first clay and water are slurried to disperse into a slurry having a solid content of 5-48 wt %; wherein said alumina source is aluminum hydroxide that can be peptized with an acid and/or alumina, relative to 15-40 parts by weight of the alumina source as $Al_2O_3$, the used amount of the first clay based on the dry weight is greater than 0 part by weight and not more than 40 parts by weight; a concentrated phosphoric acid is added to the slurry under stirring according to the weight ratio of P/Al=1-6, and the resulting mixed slurry is reacted at 50-99° C. for 15-90 minutes; wherein P in the P/Al is the weight of phosphorus as simple substance in the phosphoric acid, Al is the weight of aluminum as simple substance in the alumina source.

In the present invention, said shaping is pelleting by spray-drying and said shaping produces microspheres having a diameter of 1-150 m. The shaping operation is well known to those skilled in the art and will not be described in details herein.

The present invention also provides the catalytic cracking catalyst prepared with the above-mentioned process.

The present invention also provides the catalytic cracking auxiliary prepared with the above-mentioned process.

The present invention further provides a process for catalytically cracking a hydrocarbon oil, wherein the process comprises the hydrocarbon oil is reacted by contacting the catalytic cracking agent (catalytic cracking catalyst or catalytic cracking auxiliary) according to the present invention under the catalytic cracking condition.

The present invention further provides a process for catalytically cracking a hydrocarbon oil, wherein the process comprises the hydrocarbon oil is reacted by contacting a mixture containing the catalytic cracking auxiliary of the present invention and the catalytic cracking catalyst of the present invention; in the mixture, the content of the catalytic cracking auxiliary is 0.1-30 wt %.

The catalytic cracking condition includes: the reaction temperature is 500-800° C.; the hydrocarbon oil is one or more selected from crude oil, naphtha, gasoline, atmospheric residue, vacuum residue, atmospheric gas oil, vacuum gas oil, straight-run gas oil, propane light/heavy deasphalted oil, coker gas oil and coal liquefication product.

The present invention further provides a preparation system of a catalytic cracking agent (a catalytic cracking catalyst or a catalytic cracking auxiliary), which system is mainly composed of a phosphorus-modification device, a raw material mixing device, a shaping device, and a pressurized hydrothermal calcining device.

The phosphorus-modification device is used for the operation of impregnation-exchanging the molecular sieve to be phosphorus-modified with a solution of a phosphorus-containing compound, and comprises an equipment for introducing the solution of the phosphorus-containing compound; the raw material mixing device receives raw materials, and the raw materials include: an impregnation-treated (e.g. impregnation-exchanged) phosphorus-modified molecular sieve obtained from the phosphorus-modification device; a phosphorus-aluminum inorganic binder from a treatment device of phosphorus-aluminum inorganic binder; optionally a non-phosphorus-modified molecular sieve (e.g., an FAU-structured molecular sieve, such as a Y-type molecular sieve); and optionally a clay; said shaping device can be a device of shaping by spray-drying; and said pressurized hydrothermal calcining device is provided with an aqueous solution inlet and a gas pressurization joint to meet the conditions for the pressurized hydrothermal calcination of the shaped bodies.

The schematic flow chart of the preparation process of the catalytic cracking catalyst of the present invention is shown in FIG. 3. It can be seen from FIG. 3 that in the phosphorus-modification device of the MFI structure molecular sieve, the phosphorus-modified MFI-structured molecular sieve is obtained through impregnation-exchanging the MFI-structured molecular sieve with an aqueous solution containing phosphorus; in the raw material mixing device, the phosphorus-modified MFI-structured molecular sieve, the Y-type molecular sieve, the inorganic binder and the optionally-added second clay are mixed and slurried, and then shaped (for example, by spray-drying); the resulting shaped bodies are subjected to a hydrothermal calcining treatment in an atmosphere condition where an external pressure is applied and water is externally added.

The schematic flow chart of the preparation process of the catalytic cracking auxiliary of the present invention is shown in FIG. 4. It can be seen from FIG. 4 that in the phosphorus-modification device of the MFI structure molecular sieve, the phosphorus-modified MFI-structured molecular sieve is obtained through the impregnation treatment of the MFI-structured molecular sieve with an aqueous solution containing phosphorus; in the raw material mixing device, the raw materials including the phosphorus-modified MFI-structured molecular sieve, the inorganic binder, the optionally-added second clay and the like are mixed and slurried, and then shaped (for example, by spray-drying); the resulting shaped bodies are subjected to a pressurized hydrothermal calcining treatment in an atmosphere condition where an external pressure is applied and water is externally added.

In the present invention, the amounts such as percentages are by weight unless otherwise indicated.

In the present invention, unless otherwise specified, the sum of the weight percentages of the components of the composition is 100 wt %.

In the present invention, the D value represents the uniformity of distribution of phosphorus atoms in the catalyst or the auxiliary. The closer the D value is to 100%, the more uniform the distribution. Specifically, any section of a catalytic cracking agent (usually in the shape of microspheres, e.g. having a diameter of 1-150 μm) is randomly selected, 20 small squares with a side length of 10 nm on said section are selected, and the phosphorus content (number of atoms/number of atoms) within each small square is obtained through electron probe microanalysis (EPMA), the ratio of the lowest value of the 20 phosphorus contents to the average value of the 20 phosphorus contents is taken as the d value of the section, and the average value of the d values of 5 sections with a spacing greater than 50 nm between each other is taken as the D value of the catalytic cracking agent.

The preparation process provided by the present invention optimizes and shortens the flow process for preparing the catalytic cracking catalyst or the catalytic cracking auxiliary, which can reduce the production cost, and the catalytic cracking catalyst or the catalytic cracking auxiliary provided by the present invention has an excellent cracking conversion, an excellent lower carbon olefin yield, and a higher liquefied gas yield in the catalytic cracking reaction of petroleum hydrocarbons.

The present invention provides the following technical solutions:

1. A process for preparing a catalytic cracking catalyst, which is characterized in that the process comprises mixing a phosphorus-modified MFI-structured molecular sieve, a Y-type molecular sieve, an inorganic binder and an optionally added second clay and slurrying and shaping into shape bodies, a hydrothermal calcining treatment is performed on the shaped bodies under an atmosphere condition in which an external pressure is applied and an aqueous solution is externally added; the phosphorus-modified MFI-structured molecular sieve is obtained through contacting an MFI-structured molecular sieve having a temperature of 0-150° C. with an aqueous solution of a phosphorus-containing compound having a temperature of 0-150° C. by impregnation; Said hydrothermal calcining treatment is performed at a temperature of 200-800° C. under a gauge pressure of 0.01-1.0 MPa in an atmosphere containing 1-100% water vapor.

2. The preparation process according to technical solution 1, wherein on the dry basis, the catalytic cracking catalyst contains 1-25 wt % of Y-type molecular sieve, 5-50 wt % of phosphorus-modified MFI-structured molecular sieve, 1-60 wt % of an inorganic binder and optionally 0-60 wt % of a second clay.

3. The preparation process according to technical solution 1, wherein said Y-type molecular sieve is selected from at least one of a PSRY molecular sieve, a rare earth-containing PSRY molecular sieve, an USY molecular sieve, a rare earth-containing USY molecular sieve, a REY molecular sieve, a REHY molecular sieve and an HY molecular sieve.

4. The preparation process according to technical solution 1 or 2, wherein the inorganic binder is selected from or comprises at least one of pseudo-boehmite, alumina sol, silica-alumina sol, water glass and phosphorus-aluminum inorganic binder; preferably contains a phosphorus-aluminum inorganic binder, more preferably is a phosphorus-aluminum inorganic binder.

5. The preparation process according to technical solution 4, wherein the phosphorus-aluminum inorganic binder is a phosphorus aluminate binder and/or a first clay-containing phosphorus-aluminum inorganic binder.

6. The preparation process according to technical solution 5, wherein the first clay-containing phosphorus-aluminum inorganic binder is based on the dry basis, the first clay-containing phosphorus-aluminum inorganic binder contains 15-40 wt % of an aluminum component (as $Al_2O_3$), 45-80 wt % of a phosphorus component (as $P_2O_5$) and greater than 0 and not more than 40 wt % of a first clay, and the first clay-containing phosphorus-aluminum inorganic binder has a P/Al weight ratio of 1.0-6.0, a pH of 1-3.5, and a solid content of 15-60 wt %; the first clay comprises at least one of kaolin, sepiolite, attapulgite, rectorite, montmorillonite and diatomite.

7. The preparation process according to technical solution 1, wherein the second clay is selected from at least one of kaolin, sepiolite, attapulgite, rectorite, montmorillonite, giagerite, halloysite, hydrotalcite, bentonite and diatomite.

8. The preparation process according to technical solution 1, wherein based on the total amount of said catalytic cracking catalyst, the inorganic binder comprises on the dry basis 3-39 wt % of a phosphorus-aluminum inorganic binder and 1-30 wt % of at least one inorganic binder selected from pseudo-boehmite, alumina sol, silica alumina sol and water glass.

9. The preparation process according to technical solution 5, the process further comprises: the first clay-containing phosphorus-aluminum inorganic binder is prepared with the following steps: an alumina source, a first clay and water are slurried to disperse into a slurry having a solid content of 5-48 wt %; wherein said alumina source is aluminum hydroxide that can be peptized with an acid and/or alumina, relative to 15-40 parts by weight of the alumina source as $Al_2O_3$, the used amount of the first clay based on the dry weight is greater than 0 part by weight and not more than 40 parts by weight; a concentrated phosphoric acid is added to the slurry under stirring according to the weight ratio of P/Al=1-6, and the resulting mixed slurry is reacted at 50-99° C. for 15-90 minutes; wherein P in the P/Al is the weight of phosphorus as simple substance in the phosphoric acid, Al is the weight of aluminum as simple substance in the alumina source.

10. The preparation process according to technical solution 1, wherein said shaping is pelleting by spray-drying.

11. The preparation process according to technical solution 1, wherein the atmosphere condition has a gauge pressure of 0.01-1.0 MPa, preferably 0.3-0.6 MPa and contains 30%-100% water vapor, preferably 60-100% water vapor; said hydrothermal calcining treatment is performed at 200-800° C., preferably 300-500° C.

12. The preparation process according to technical solution 1, wherein the phosphorus-containing compound is selected from an organic phosphorus compound and/or an inorganic phosphorus compound.

13. The preparation process according to technical solution 12, wherein the organic phosphorus compound is selected from trimethyl phosphate, triphenylphosphine, trimethyl phosphite, tetrabutylphosphonium bromide, tetrabutylphosphonium chloride, tetrabutylphosphonium hydroxide, triphenylethylphosphonium bromide, triphenylbutylphosphonium bromide, triphenylbenzylphosphonium bromide, hexamethylphosphoric triamide, dibenzyl diethylphosphoramidite, and 1, 3-bis((triethyl-phosphaneyl) methyl)benzene; the inorganic phosphorus compound is selected from phosphoric acid, ammonium hydrogen phosphate, diammonium hydrogen phosphate, ammonium phosphate, and boron phosphate.

14. The preparation process according to technical solution 1, wherein in the MFI structure molecular sieve, $Na_2O$<0.1 wt %.

15. The preparation process according to technical solution 1, wherein the phosphorus-modified MFI-structured molecular sieve is a micropore ZSM-5 molecular sieve or a hierarchical ZSM-5 molecular sieve.

16. The catalytic cracking catalyst according to technical solution 15, wherein the micropore ZSM-5 molecular sieve has a silica/alumina molar ratio of 15-1000, preferably 20-200; and the hierarchical ZSM-5 molecular sieve has a proportion of the mesopore volume relative to the total pore volume of greater than 10%, an average pore size of 2-20 nm, and a silica/alumina molar ratio of 15-1000, preferably 20-200.

17. The preparation process according to technical solution 1, wherein the molar ratio of the phosphorus-containing compound (as phosphorus) to the MFI-structured molecular sieve (as aluminum) is 0.01-2; preferably, 0.1-1.5; more preferably, 0.2-1.5.

18. The preparation process according to technical solution 1, wherein the contacting is performed at a weight ratio of water/molecular sieve of 0.5-1, at a temperature of 50-150° C., preferably 70-130° C. for 0.5-40 hours.

19. A catalytic cracking catalyst obtained from the preparation process according to any of technical solutions 1-18.

20. A process for catalytically cracking a hydrocarbon oil, which is characterized in that the process comprises: the hydrocarbon oil is reacted by contacting the catalytic cracking catalyst according to technical solution 19 under a catalytic cracking condition. 21. The process according to technical solution 20, wherein the catalytic cracking condition includes: the reaction temperature is 500-800° C.; the hydrocarbon oil is one or more selected from crude oil, naphtha, gasoline, atmospheric residue, vacuum residue, atmospheric gas oil, vacuum gas oil, straight-run gas oil, propane light/heavy deasphalted oil, coker gas oil and coal liquefication product. 22. A preparation system of a catalytic cracking agent, which is characterized in that the system is mainly composed of a phosphorus-modification device of the MFI-structured molecular sieve, a raw material mixing device, a shaping device, and a pressurized hydrothermal calcining device.

23. The preparation system according to technical solution 22, wherein the phosphorus-modification device of the MFI structure molecular sieve comprises an equipment for introducing a solution of a phosphorus-containing compound.

24. The preparation system according to technical solution 22, wherein the raw material mixing device receives raw materials for preparing the catalyst, including: an impregnation-exchanged MFI-structured molecular sieve obtained from the phosphorus-modification device of the MFI-structured molecular sieve, a phosphorus-aluminum inorganic binder from the treatment device of phosphorus-aluminum inorganic binder, a Y-type molecular sieve, and an optionally added clay.

25. The preparation system according to technical solution 22, wherein said shaping device is a device of shaping by spray-drying.

26. The preparation system according to technical solution 22, wherein said pressurized hydrothermal calcining device is provided with a water inlet and a gas pressurization joint.

27. A process for preparing a catalytic cracking auxiliary, which is characterized in that the process comprises: mixing a phosphorus-modified MFI-structured molecular sieve obtained through contacting a MFI-structured molecular sieve having a temperature of 0-150° C. with an aqueous solution of a phosphorus-containing compound having a temperature of 0-150° C. by impregnation, an inorganic binder, and an optionally added second clay, slurrying the resulting mixture, and shaping into shaped bodies; a hydrothermal calcining treatment is performed on the shaped bodies under an atmosphere condition in which an external pressure is applied and an aqueous solution is externally added; said hydrothermal calcining treatment is performed at a temperature of 200-800° C. under a gauge pressure of 0.01-1.0 MPa in an atmosphere containing 1-100% water vapor.

28. The preparation process according to technical solution 27, wherein on the dry basis, the catalytic cracking auxiliary contains 5-75 wt % of a phosphorus-modified MFI-structured molecular sieve, 1-40 wt % of an inorganic binder and 0-65 wt % of a second clay.

29. The preparation process according to technical solution 27, wherein the phosphorus-containing compound is selected from an organic phosphorus compound and/or an inorganic phosphorus compound.

30. The preparation process according to technical solution 27, wherein the organic phosphorus compound is selected from trimethyl phosphate, triphenylphosphine, trimethyl phosphite, tetrabutylphosphonium bromide, tetrabutylphosphonium chloride, tetrabutylphosphonium hydroxide, triphenylethylphosphonium bromide, triphenylbutylphosphonium bromide, triphenylbenzylphosphonium bromide, hexamethylphosphoric triamide, dibenzyl diethylphosphoramidite, and 1, 3-bis((triethyl-phosphaneyl) methyl)benzene; the inorganic phosphorus compound is selected from phosphoric acid, ammonium hydrogen phosphate, diammonium hydrogen phosphate, ammonium phosphate, and boron phosphate.

31. The preparation process according to technical solution 27, wherein in the MFI structure molecular sieve, $Na_2O<0.1$ wt %.

32. The preparation process according to technical solution 27, wherein the phosphorus-modified MFI-structured molecular sieve is a micropore ZSM-5 molecular sieve or a hierarchical ZSM-5 molecular sieve.

33. The preparation process according to technical solution 32, wherein the micropore ZSM-5 molecular sieve has a molar ratio of silica to alumina of 15-1000, preferably 20-200; the hierarchical ZSM-5 molecular sieve has a proportion of the mesopore volume relative to the total pore volume of greater than 10%, an average pore size of 2-20 nm, and a molar ratio of silica to alumina of 15-1000, preferably 20-200.

34. The preparation process according to technical solution 27, wherein the molar ratio of the phosphorus-containing compound (as phosphorus) to the MFI-structured molecular sieve (as aluminum) is 0.01-2; preferably, 0.1-1.5; more preferably, 0.2-1.5.

35. The preparation process according to technical solution 27, wherein said impregnation treatment is performed at a weight ratio of water/molecular sieve of 0.5-1 at a temperature of 50-150° C., preferably 70-130° C. for 0.5-40 hours.

36. The preparation process according to technical solution 27, wherein the inorganic binder is selected from or comprises at least one of pseudo-boehmite, alumina sol, silica-alumina sol, water glass and phosphorus-aluminum inorganic binder; the preferred inorganic binder contains a phosphorus-aluminum inorganic binder, the more preferable inorganic binder is a phosphorus-aluminum inorganic binder.

37. The preparation process according to technical solution 36, wherein the phosphorus-aluminum inorganic binder is a phosphorus aluminate binder and/or a first clay-containing phosphorus-aluminum inorganic binder.

38. The preparation process according to technical solution 37, wherein the first clay-containing phosphorus-aluminum inorganic binder is based on the dry basis, the first clay-containing phosphorus-aluminum inorganic binder contains 15-40 wt % of an aluminum component (as $Al_2O_3$), 45-80 wt % of a phosphorus component (as $P_2O_5$) and greater than 0 and not more than 40 wt % of a first clay, and the first clay-containing phosphorus-aluminum inorganic binder has a P/Al weight ratio of 1.0-6.0, a pH of 1-3.5, and a solid content of 15-60 wt %; the first clay comprises at least one of kaolin, sepiolite, attapulgite, rectorite, montmorillonite and diatomite.

39. The preparation process according to technical solution 27, wherein the second clay is selected from at least one of kaolin, sepiolite, attapulgite, rectorite, montmorillonite, giagerite, halloysite, hydrotalcite, bentonite and diatomite.

40. The preparation process according to technical solution 36, wherein based on the total amount of the catalytic cracking auxiliary, the inorganic binder comprises on the dry basis 3-39 wt % of the phosphorus-aluminum inorganic binder and 1-30 wt % of at least one inorganic binder selected from pseudo-boehmite, alumina sol, silica alumina sol and water glass.

41. The preparation process according to technical solution 37, the process further comprises: the first clay-containing phosphorus-aluminum inorganic binder is prepared with the following steps: an alumina source, a first clay and water are slurried to disperse into a slurry having a solid content of 5-48 wt %; wherein said alumina source is aluminum hydroxide that can be peptized with an acid and/or alumina, relative to 15-40 parts by weight of the alumina source as $Al_2O_3$, the used amount of the first clay based on the dry weight is greater than 0 part by weight and not more than 40 parts by weight; a concentrated phosphoric acid is added to the slurry under stirring according to the weight ratio of P/Al=1-6, and the resulting mixed slurry is reacted at 50-99° C. for 15-90 minutes; wherein P in the P/Al is the weight of phosphorus as simple substance in the phosphoric acid, Al is the weight of aluminum as simple substance in the alumina source.

42. The preparation process according to technical solution 27, wherein said shaping is shaping by spray-drying.

43. The preparation process according to technical solution 27, wherein the atmosphere condition has a gauge pressure of 0.01-1.1 MPa, preferably 0.3-0.6 MPa and contains 30%-100% water vapor, preferably 60-100% water vapor; said hydrothermal calcining treatment is performed at 200-800° C., preferably 300-500° C.

44. A catalytic cracking auxiliary obtained from the preparation process according to any of technical solutions 27-43.

45. A process for catalytically cracking a hydrocarbon oil, which is characterized in that the process comprises: the hydrocarbon oil is reacted by contacting the catalytic cracking auxiliary according to technical solution 44 under a catalytic cracking condition.

46. The process according to technical solution 45, wherein the process comprises: the hydrocarbon oil is reacted by contacting a catalyst mixture containing the catalytic cracking auxiliary and the catalytic cracking catalyst under a catalytic cracking condition; in the catalyst mixture, the content of the catalytic cracking auxiliary is 0.1-30 wt %.

47. The process according to technical solution 45 or 46, wherein the catalytic cracking condition includes: the reaction temperature is 500-800° C.; the hydrocarbon oil is one or more selected from crude oil, naphtha, gasoline, atmospheric residue, vacuum residue, atmospheric gas oil, vacuum gas oil, straight-run gas oil, propane light/heavy deasphalted oil, coker gas oil and coal liquefication product.

48. A preparation system of a catalytic cracking auxiliary, which is characterized in that the system is mainly composed of a phosphorus-modification device of the MFI-structured molecular sieve, a raw material mixing device, a shaping device, and a pressurized hydrothermal calcining device.

49. The preparation system according to technical solution 48, wherein the phosphorus-modification device of the MFI structure molecular sieve comprises an equipment for introducing a solution of a phosphorus-containing compound.

50. The preparation system according to technical solution 48, wherein the raw material mixing device receives raw materials for preparing the auxiliary, including: an impregnation-treated MFI-structured molecular sieve obtained from the phosphorus-modification device of the MFI-structured molecular sieve, a phosphorus-aluminum inorganic binder from the treatment device of phosphorus-aluminum inorganic binder, and an optionally added clay.

51. The preparation system according to technical solution 48, wherein said shaping device is a device of shaping by spray-drying.

52. The preparation system according to technical solution 48, wherein said pressurized hydrothermal calcining device is provided with an aqueous solution inlet and a gas pressurization joint.

The present invention also provides a group of the following technical solutions:

1. A catalytic cracking agent, having an active component consisting of a phosphorus-modified molecular sieve and a non-phosphorus-modified molecular sieve or only consisting of a phosphorus-modified molecular sieve, with the electron probe microanalysis (EPMA),
    the D value of phosphorus in the catalytic cracking agent is ≥65%, preferably ≥68%, provided that the active component consists of the phosphorus-modified molecular sieve and the non-phosphorus-modified molecular sieve, or
    the D value of phosphorus in the catalytic cracking agent is ≥82%, preferably ≥84%, provided that the active component only consists of the phosphorus-modified molecular sieve;

For example, the D value is determined by randomly selecting any section of a catalytic cracking agent (usually in the shape of microspheres, e.g. having a diameter of 1-150 μm), selecting 20 small squares with a side length of 10 nm on said section, and obtaining the phosphorus content (number of atoms/number of atoms) within each small square through electron probe microanalysis (EPMA), taking the ratio of the lowest value of the 20 phosphorus contents to the average value of the 20 phosphorus contents as the d value of the section, and taking the average value of the d values of 5 sections with a spacing greater than 50 nm between each other as the D value of the catalytic cracking agent.

Specifically, the upper limit of the D value of phosphorus in the catalytic cracking agent is 100%. the D value of phosphorus in the catalytic cracking agent is <100%, for example <90%, e.g. <80%, provided that the active component consists of the phosphorus-modified molecular sieve and the non-phosphorus-modified molecular sieve, or
    the D value of phosphorus in the catalytic cracking agent is <100%, for example <99%, e.g. <98%, provided that the active component only consists of the phosphorus-modified molecular sieve.

2. The catalytic cracking agent according to any of previous solutions, wherein
    said phosphorus-modified molecular sieve is a phosphorus-modified MFI-structured molecular sieve, for example a phosphorus-modified ZSM-5 molecular sieve;
    said non-phosphorus-modified molecular sieve is a FAU-structured molecular sieve, for example, a Y-type molecular sieve.

3. The catalytic cracking agent according to any of solutions 1-2, wherein said catalytic cracking agent is a catalytic cracking catalyst, having an active component consisting of a phosphorus-modified molecular sieve (for example a phosphorus-modified MFI-structured molecular sieve, such as a phosphorus-modified ZSM-5 molecular sieve) and a non-phosphorus-modified molecular sieve (for example a FAU-structured molecular sieve, such as a Y-type molecular sieve), with the electron probe microanalysis (EPMA), the D-value of the phosphorus of the catalyst is ≥65%, preferably ≥68%.

4. The catalytic cracking agent according to any of solutions 1-2, wherein said catalytic cracking agent is a catalytic cracking auxiliary, having an active component consisting of a phosphorus-modified molecular sieve, with the electron probe microanalysis (EPMA), the D-value of phosphorus of the auxiliary is ≥82%, preferably ≥84%.

5. The catalytic cracking agent according to any of solutions 1-2, wherein on the dry basis, said catalytic cracking agent contains:
    1-25 wt % of a non-phosphorus-modified molecular sieve;
    5-50 wt % of a phosphorus-modified molecular sieve;
    1-60 wt % of an inorganic binder; and
    optionally, 0-60 wt % of a second clay.

6. The catalytic cracking agent according to any of solutions 1-2, wherein on the dry basis, said catalytic cracking agent contains:
    5-75 wt % of a phosphorus-modified molecular sieve (free of non-phosphorus-modified molecular sieve);
    1-40 wt % of an inorganic binder; and
    optionally, 0-65 wt % of a second clay.

7. The catalytic cracking agent according to any of the previous solutions, wherein said non-phosphorus-modified molecular sieve is at least one of a PSRY molecular sieve, a rare earth-containing PSRY molecular sieve, an USY molecular sieve, a rare earth-containing USY molecular sieve, a REY molecular sieve, a REHY molecular sieve and an HY molecular sieve.

8. The catalytic cracking agent according to any of the previous solutions, wherein the inorganic binder comprises at least one of pseudo-boehmite, alumina sol, silica-alumina sol, water glass and phosphorus-aluminum inorganic binder;
    preferably, the inorganic binder contains a phosphorus-aluminum inorganic binder,
    more preferably, the inorganic binder is a phosphorus-aluminum inorganic binder.

9. The catalytic cracking agent according to any of the previous solutions, wherein the phosphorus-aluminum inorganic binder is a phosphorus aluminate binder and/or a first clay-containing phosphorus-aluminum inorganic binder.

10. The catalytic cracking agent according to any of the previous solutions, wherein the first clay-containing phosphorus-aluminum inorganic binder is based on the dry basis, the first clay-containing phosphorus-aluminum inorganic binder contains 15-40 wt % of an aluminum component (as $Al_2O_3$), 45-80 wt % of a phosphorus component (as $P_2O_5$) and greater than 0 and not more than 40 wt % of a first clay, and the first clay-containing phosphorus-aluminum inorganic binder has a P/Al weight ratio of 1.0-6.0, a pH of 1-3.5, and a solid content of 15-60 wt %; the first clay comprises at least one of kaolin, sepiolite, attapulgite, rectorite, montmorillonite and diatomite.

11. The catalytic cracking agent according to any of the previous solutions, wherein the second clay is selected from at least one of kaolin, sepiolite, attapulgite, rectorite, montmorillonite, glagerite, halloysite, hydrotalcite, bentonite and diatomite.

12. The catalytic cracking agent according to any of the previous solutions, wherein based on the total amount of said catalytic cracking catalyst, the inorganic binder comprises, on the dry basis, 3-39 wt % of a phosphorus-aluminum inorganic binder and 1-30 wt % of at least one inorganic binder selected from pseudo-boehmite, alumina sol, silica alumina sol and water glass.

13. A process for preparing the catalytic cracking agent according to any of the precedent solutions, which is characterized in that the process comprises:
   (1) mixing the following components as raw material and slurrying the raw material, and shaping into shaped bodies:
   a phosphorus-modified molecular sieve,
   optionally, a non-phosphorus-modified molecular sieve,
   an inorganic binder, and
   optionally, a second clay;
   (2) a hydrothermal calcining treatment is performed on the shaped bodies under an atmosphere condition in which an external pressure is applied and an aqueous solution is externally added;
   said phosphorus-modified molecular sieve is obtained through contacting a molecular sieve to be phosphorus-modified having a temperature of 0-150° C. with an aqueous solution of a phosphorus-containing compound having a temperature of 0-150° C. by impregnation;
   said hydrothermal calcining treatment is performed under a gauge pressure of 0.01-1.0 MPa at a temperature of 200-800° C. in an atmosphere of 100% water vapor or in an air atmosphere having a moisture content of at least 1%.

14. The process according to any of the previous solutions, wherein said molecular sieve to be phosphorus-modified is a micropore ZSM-5 molecular sieve or a hierarchical ZSM-5 molecular sieve; preferably, the micropore ZSM-5 molecular sieve has a silica/alumina molar ratio of 15-1000, preferably 20-200;
   preferably, the hierarchical ZSM-5 molecular sieve has a proportion of the mesopore volume relative to the total pore volume of greater than 10%, an average pore size of 2-20 nm, and a silica/alumina molar ratio of 15-1000, preferably 20-200.

15. The process according to any of the previous solutions, wherein the molar ratio of the phosphorus-containing compound (as phosphorus) to the molecular sieve to be phosphorus-modified (as aluminum) is 0.01-2; preferably, 0.1-1.5; more preferably, 0.2-1.5.

16. The process according to any of the previous solutions, wherein the phosphorus-containing compound is selected from an organic phosphorus compound and/or an inorganic phosphorus compound;
   preferably, the organic phosphorus compound is selected from trimethyl phosphate, triphenylphosphine, trimethyl phosphite, tetrabutylphosphonium bromide, tetrabutylphosphonium chloride, tetrabutylphosphonium hydroxide, triphenylethylphosphonium bromide, triphenylbutylphosphonium bromide, triphenylbenzylphosphonium bromide, hexamethylphosphoric triamide, dibenzyl diethylphosphoramidite, and 1, 3-bis((triethyl-phosphaneyl)methyl)benzene;
   preferably, the inorganic phosphorus compound is selected from phosphoric acid, ammonium hydrogen phosphate, diammonium hydrogen phosphate, ammonium phosphate, and boron phosphate.

17. The process according to any of the previous solutions, wherein in said molecular sieve to be phosphorus-modified, $Na_2O<0.1$ wt %.

18. The process according to any of the previous solutions, the process further comprises: the first clay-containing phosphorus-aluminum inorganic binder is prepared with the following steps: an alumina source, a first clay and water are slurried to disperse into a slurry having a solid content of 5-48 wt %; wherein said alumina source is aluminum hydroxide that can be peptized with an acid and/or alumina, relative to 15-40 parts by weight of the alumina source as $Al_2O_3$, the used amount of the first clay based on the dry weight is greater than 0 part by weight and not more than 40 parts by weight; a concentrated phosphoric acid is added to the slurry under stirring according to the weight ratio of P/Al=1-6, and the resulting mixed slurry is reacted at 50-99° C. for 15-90 minutes; wherein P in the P/Al is the weight of phosphorus as simple substance in the phosphoric acid, Al is the weight of aluminum as simple substance in the alumina source.

19. The process according to any of the previous solutions, wherein said shaping is pelleting by spray-drying.

20. The process according to any of the previous solutions, wherein the conditions of said hydrothermal calcining treatment comprise:
   gauge pressure: 0.1-0.8 MPa, preferably 0.3-0.6 MPa;
   atmosphere: an atmosphere of 100% water vapor or an air atmosphere having a moisture content of at least 30%, preferably, an atmosphere of 100% water vapor or an air atmosphere having a moisture content of at least 60%;
   temperature: 200-800° C., preferably 300-500° C.;
   the conditions of said contacting by impregnation comprise:
   the weight ratio of water/molecular sieve: 0.5-1;
   temperature: 50-150° C., preferably 70-130° C.;
   time: 0.5-40 hours.

21. A catalytic cracking agent according to any of solutions 1-12, which is prepared with the process according to any of solutions 13-20.

22. A process for catalytically cracking a hydrocarbon oil, which is characterized in that the process comprises: the hydrocarbon oil is reacted by contacting the catalytic cracking agent according to any of the previous solutions under a catalytic cracking condition.

23. The process for catalytically cracking the hydrocarbon oil according to any of the previous solutions, wherein the process comprises the hydrocarbon oil is reacted by contacting a mixture containing the catalytic cracking auxiliary according to any of the previous solutions and the catalytic cracking catalyst according to any of the previous solutions under a catalytic cracking condition; in the mixture, the content of the catalytic cracking auxiliary is 0.1-30 wt %.

24. The process for catalytically cracking the hydrocarbon oil according to any of the previous solutions, wherein
   the catalytic cracking condition includes: the reaction temperature is 500-800° C.; the hydrocarbon oil is one or more selected from crude oil, naphtha, gasoline, atmospheric residue, vacuum residue, atmospheric gas oil, vacuum gas oil, straight-run gas oil, propane light/heavy deasphalted oil, coker gas oil and coal liquefication product.

25. A preparation system of a catalytic cracking agent, which is characterized in that the system is mainly composed of a phosphorus-modification device, a raw material mixing device, a shaping device, and a pressurized hydrothermal calcining device;
   preferably, the phosphorus-modification device comprises an equipment for introducing a solution of a phosphorus-containing compound; and/or the raw material mixing device receives raw materials, and the raw materials include: an impregnation-treated (e.g. impregnation-exchanged) phosphorus-modified molecular sieve obtained from the phosphorus-modification device, a phosphorus-aluminum inorganic binder from a treatment device of phosphorus-aluminum inorganic binder; optionally a non-phosphorus-modified molecular sieve, and optionally a clay; and/or said shaping device is a device of shaping by spray-drying; and/or said pressurized hydrothermal calcining device is provided with an aqueous solution inlet and a gas pressurization joint.

DETAILED DESCRIPTION OF THE INVENTION

Figure 1:
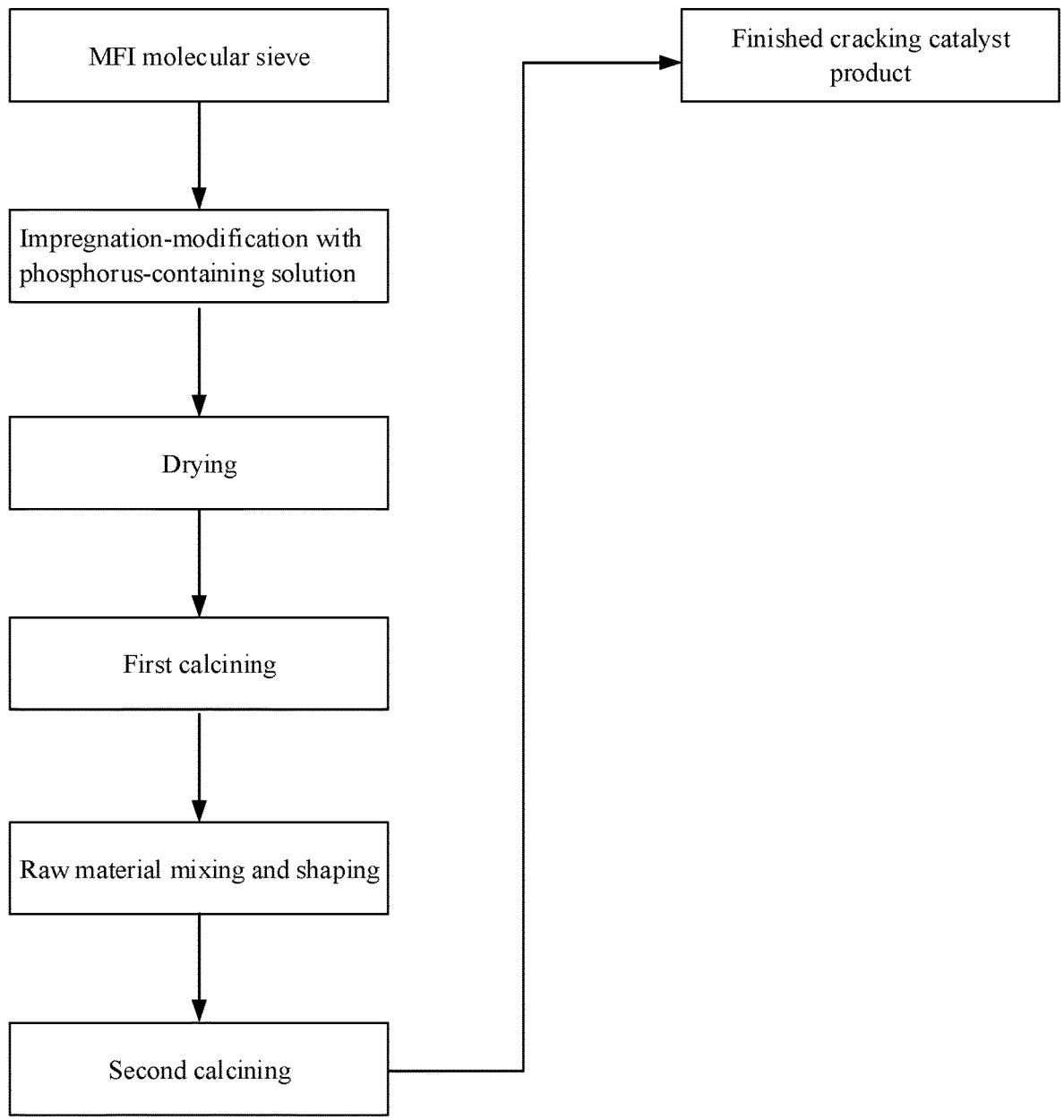
FIG. 1 is the flowchart for preparing a conventional catalyst in the prior art.
Figure 2:
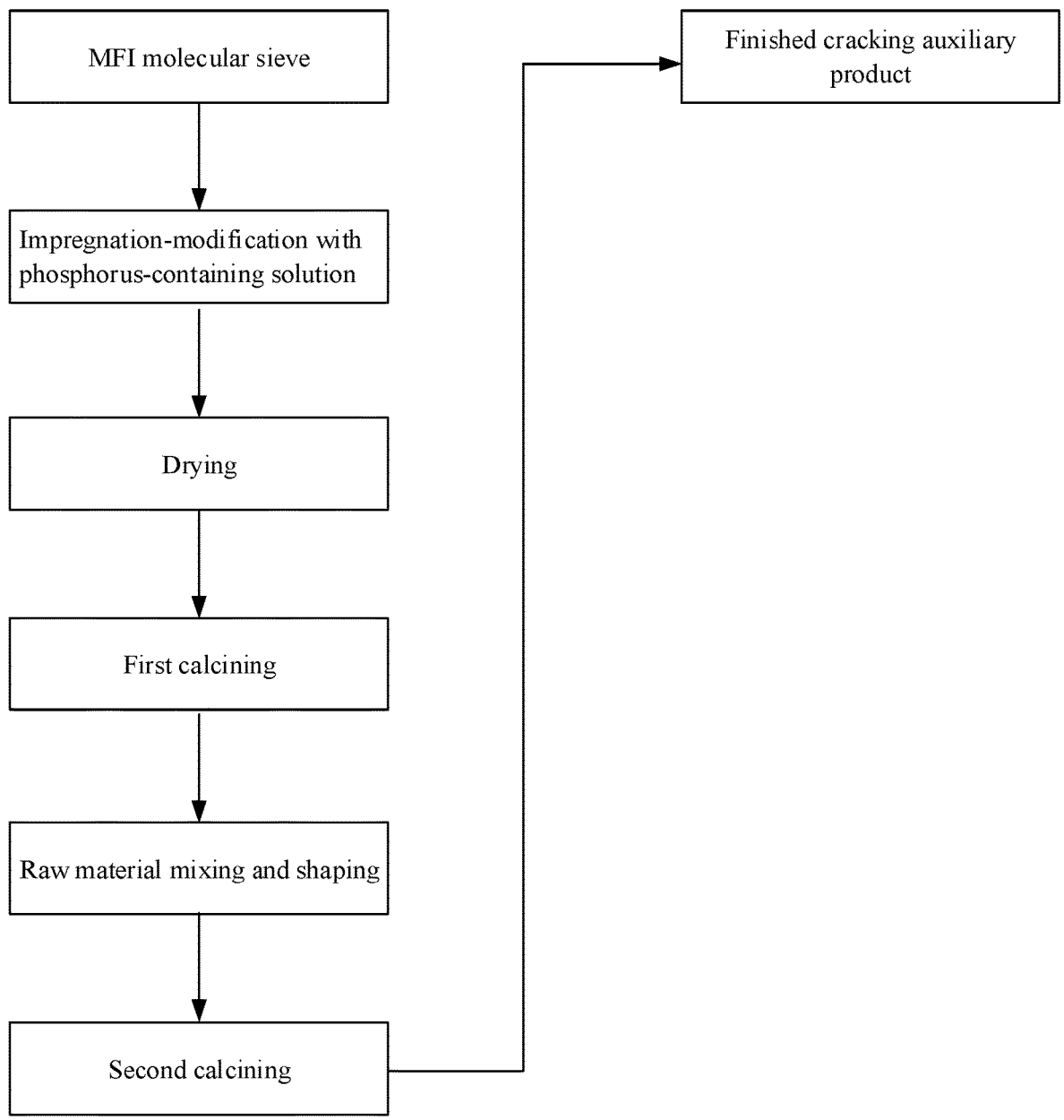
FIG. 2 is the flowchart for preparing a conventional auxiliary in the prior art.
Figure 3:
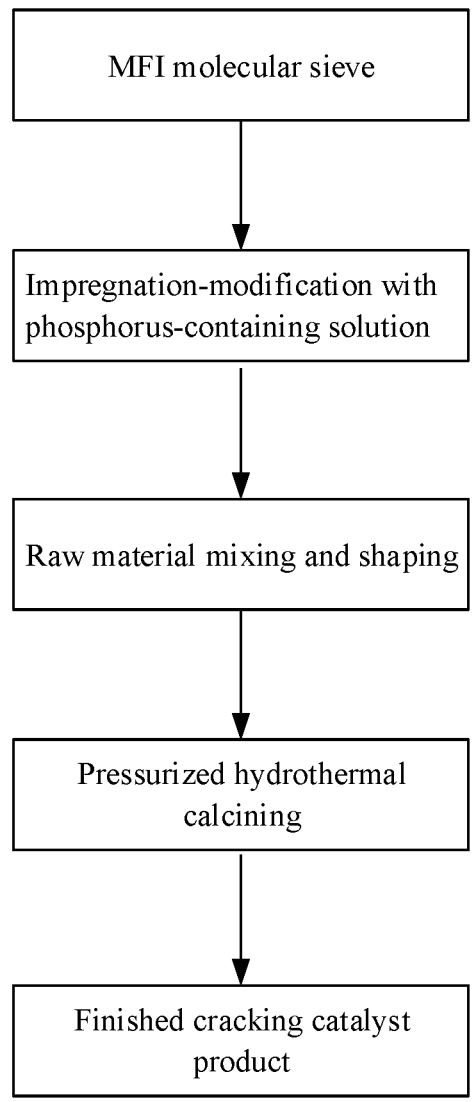
FIG. 3 is the flowchart for preparing a catalyst provided by the present invention.
Figure 4:
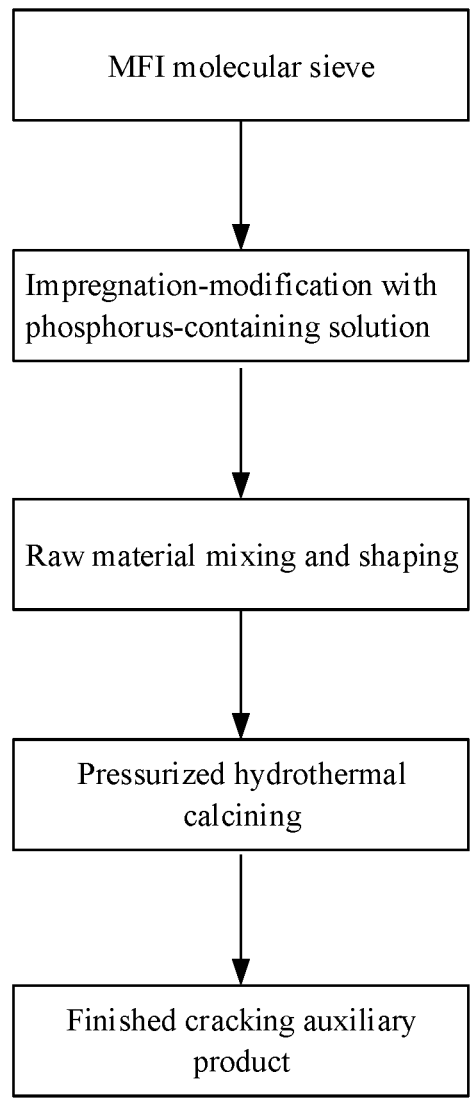
FIG. 4 is the flowchart for preparing an auxiliary provided by the present invention.

The present invention will be further described below in conjunction with specific examples, but the present invention is not limited thereby.

The instruments and reagents used in the examples of the present invention are all those commonly used by those skilled in the art unless otherwise specified.

A micro-reaction apparatus was used to evaluate the effect of the catalytic cracking catalyst or the catalytic cracking auxiliary of the present invention on the yield of lower carbon olefins in the catalytic cracking of petroleum hydrocarbons.

The prepared catalytic cracking catalyst sample/catalytic cracking auxiliary sample was subjected to the aging treatment at 800° C., 100% water vapor for 17 hours in a fixed-bed aging apparatus, and evaluated on a micro-reaction apparatus. The feedstock oil is VGO or naphtha. The evaluation condition included: the reaction temperature was 620° C., the regeneration temperature was 620° C., and the agent(catalyst/auxiliary)-oil ratio was 3.2. The micro-reactivity was measured by the ASTM D5154-2010 standard method.

EPMA (Model JXA-8230 Electron Probe Microanalyzer) was used to quantitatively analyze the D value of phosphorus in the sample section. Specifically, the D value is determined by randomly selecting 5 sections of a sample with a spacing greater than 50 nm between each other; selecting 20 squares with a side length of 10 nm on each section, and obtaining the phosphorus content (number of atoms/number of atoms) within each square through electron probe microanalysis (EPMA), taking the ratio of the lowest value of the 20 phosphorus contents to the average value of the 20 phosphorus contents as the d value of the section, and taking the average value of the d values of 5 sections as the D value of phosphorus of said sample.

The properties of some raw materials used in the Examples were as follows:

| | |
|---|---|
| Pseudo-boehmite | An industrial product produced by Shandong Aluminum Company, with a solid content of 60 wt %. |
| Alumina sol | An industrial product produced by Sinopec Catalyst Qilu Branch, and had the $Al_2O_3$ content of 21.5 wt %. |
| Silica sol | An industrial product produced by Sinopec Catalyst Qilu Branch, with a SiO2 content of 28.9 wt % and a $Na_2O$ content of 8.9%. |
| Kaolin | A kaolin special for catalytic cracking catalyst produced by Suzhou Kaolin Company, with a solid content of 78% by weight. |
| Rectorite | Produced by Hubei Zhongxiang Mingliu Rectorite Development Co., Ltd., with the quartz sand content of <3.5 wt %, the $Al_2O_3$ content of 39.0 wt %, the $Na_2O$ content of 0.03 wt %, and the solid content of 77 wt %. |
| SB aluminum hydroxide powder | Produced by Condex Corporation, Germany, with an $Al_2O_3$ content of 75 wt %. |
| γ-alumina | Produced by Condex Corporation, Germany, with an $Al_2O_3$ content of 95 wt %. |
| Hydrochloric acid | Chemically pure, with a concentration of 36-38 wt %, produced by Beijing Chemical Plant. |
| PSRY molecular sieve | An industrial product produced by Sinopec Catalyst Changling Branch, with the $Na_2O$ content of <1.5 wt %, the $P_2O_5$ content of 0.8-1.2 wt %, the unit cell constant of <2.456 nm, and the crystallinity of ≤64%. |
| HRY-1 commercial molecular sieve | An industrial product produced by Sinopec Catalyst Changling Branch, with the La2O3 content of 11-13 wt %, the unit cell constant of <2.464 nm, and the crystallinity of ≥40%. |

The phosphorus-aluminum inorganic binder, Binder 1, that was used in examples was prepared as follows: 1.91 kg of pseudo-boehmite (containing $Al_2O_3$, 1.19 kg), 0.56 kg of kaolin (0.5 kg on a dry basis) and 3.27 kg of decationized water were mixed and stirred for 30 minutes to form a slurry, and 5.37 kg of concentrated phosphoric acid (mass concentration 85%) was added to the slurry under stirring, wherein the addition rate of phosphoric acid was 0.04 kilogram phosphoric acid/min/kg alumina source. The mixture was warmed up to 70° C., and then reacted at this temperature for 45 minutes to produce the phosphorus-aluminum inorganic binder. The material proportions were shown in Table 1.

Phosphorus-aluminum inorganic binders Binder 2, Binder 3, and Binder 4 were also prepared according to the above-mentioned method, the difference lies in that the material proportions were different, and the material proportions were shown in Table 1.

TABLE 1

| | Inorganic binder No. | | | |
|---|---|---|---|---|
| | Binder 1 | Binder 2 | Binder 3 | Binder 4 |
| Pseudo-boehmite, kg | 1.91 | | | 1.60 |
| $Al_2O_3$, kg | 1.19 | | | 1.00 |
| SB, kg | | | 0.94 | |

TABLE 1-continued

| | Inorganic binder No. | | | |
|---|---|---|---|---|
| | Binder 1 | Binder 2 | Binder 3 | Binder 4 |
| $Al_2O_3$, kg | | 0.70 | | |
| $\gamma\text{-}Al_2O_3$, kg | | | 0.58 | |
| $Al_2O_3$, kg | | | 0.58 | |
| Rectorite, kg | | | 1.28 | 1.93 |
| Dry Basis, kg | | | 1.00 | 1.50 |
| Kaolin, kg | 0.56 | | | |
| Dry Basis, kg | 0.50 | | | |
| Phosphoric acid, kg | 5.37 | 5.36 | 4.03 | 6.50 |
| $P_2O_5$, kg | 3.31 | 3.30 | 2.92 | 4.0 |
| Decationized Water, kg | 3.27 | 6.71 | 20.18 | 4.40 |
| Total Weight, kg | 11.11 | 14.29 | 25.00 | 12.5 |
| Total Dry Basis, kg | 5.00 | 5.00 | 5.00 | 5.00 |
| Inorganic Binder Solid Content, kg/kg | 0.45 | 0.35 | 0.20 | 0.40 |
| P/Al | 2.29 | 3.89 | 4.19 | 3.30 |
| $Al_2O_3$, wt % | 23.82 | 14.00 | 11.53 | 20.00 |
| $P_2O_5$, wt % | 66.18 | 66.00 | 58.47 | 80.00 |
| First Clay, wt % | 10.00 | 20.00 | 30.00 | 0.00 |
| pH | 2.20 | 2.37 | 1.78 | 2.46 |

TABLE 2

| Item | Feedstock oil |
|---|---|
| Density (20° C.), g/cm$^3$ | 0.9334 |
| Refraction (70° C.) | 1.5061 |
| SARA, m % | |
| Saturates | 55.6 |
| Aromatics | 30 |
| Resins | 14.4 |
| Asphaltenes | <0.1 |
| freezing point, ° C. | 34 |
| Metal contents, ppm | |
| Ca | 3.9 |
| Fe | 1.1 |
| Mg | <0.1 |
| Na | 0.9 |
| Ni | 3.1 |
| Pb | <0.1 |
| V | 0.5 |
| Cm % | 86.88 |
| Hm % | 11.94 |
| Sm % | 0.7 |
| Carbon Residue m % | 1.77 |

Example F1.X to Example F24.X (X=1 or 2, the same below) provided the catalytic cracking catalysts of the present invention, and Comparative Example F1 to Comparative Example F17 illustrated the catalytic cracking catalysts for comparison. Among them, the MFI-structured molecular sieves in Example F1.X to Example F10.X were micropore ZSM-5 molecular sieves, and the MFI-structured molecular sieves in Example F11.X to Example F20.X were hierarchical ZSM-5 molecular sieves. Comparative Example F8 was a comparative catalytic cracking catalyst containing the micropore ZSM-5 MFI-structured molecular sieve prepared by the prior art, and Comparative Example F16 was a comparative catalytic cracking catalyst containing the hierarchical ZSM-5 MFI-structured molecular sieve prepared by the prior art.

Example F1.1

16.2 g of diammonium hydrogen phosphate (Tianjin Guangfu Science and Technology Development Co., Ltd., analysis pure, the same below) was dissolved in 60 g of deionized water, and the mixture was stirred for 0.5 hours to obtain an aqueous solution containing phosphorus; 113 g of HZSM-5 molecular sieve (provided by Changling Division of Sinopec Catalyst Company and having a relative crystallinity of 91.1%, a silica/alumina molar ratio of 24.1, a $Na_2O$ content of 0.039 wt %, a specific surface area of 353 m$^2$/g, and a total pore volume of 0.177 mL/g, the same below) was added to the solution and modified by impregnation, i.e., impregnated at 20° C. for 2 hours; the resulting mixture was mixed with a Y-type molecular sieve (PSRY molecular sieve), kaolin and pseudo-boehmite; decationized water and alumina sol were added and the resulting mixture was stirred for 120 minutes to obtain a slurry with a solid content of 30 wt %; hydrochloric acid was added to adjust the pH value of the slurry to 3.0; then the mixture continued to be stirred for 45 minutes; then the phosphorus-aluminum inorganic binder, Binder 1, was added, and the resulting mixture was stirred for 30 minutes; the resulting slurry was shaped by spray-drying to produce microspheres (having a diameter of 1-150 m); the microspheres were treated at 500° C. for 0.5 hours in a condition where an external pressure was applied and water was externally added, i.e. under a pressure of 0.5 MPa in a 50% water vapor atmosphere to produce a catalytic cracking catalyst sample, which was denoted as CFZY1.1, the composition of which comprised 40% of phosphorus-modified ZSM-5 molecular sieve, 10% of PSRY molecular sieve, 23% of kaolin, 18% of Binder 1, 5% of pseudo-boehmite (as $Al_2O_3$), and 4% of alumina sol (as $Al_2O_3$).

A fixed bed micro-reaction apparatus was used to evaluate the reaction performances of a 100% equilibrium catalyst and an equilibrium catalyst to which the catalytic cracking catalyst CFZY1.1 prepared in Example F1.1 was incorporated, in order to illustrate the catalytic cracking reaction effect of the catalytic cracking catalyst provided in the present disclosure.

The catalyst CFZY1.1 was aged at 800° C. in a 100% water vapor atmosphere for 17 hours. The aged CFZY1.1 was mixed with an industrial FCC equilibrium catalyst (an FCC equilibrium catalyst with the industry brand of DVR-3 having a light oil micro-activity of 63). A mixture of the equilibrium catalyst and the catalyst was loaded into the fixed-bed micro-reaction reactor, and the feedstock oil shown in Table 2 was catalytically cracked. The evaluation condition included: the reaction temperature was 620° C., the regeneration temperature was 620° C., and the catalyst-oil ratio was 3.2. Table 3 provided the reaction results, including the blank test agent.

Example F1.2

This example was performed in the same manner as Example F1.1, except for the preparation of the phosphorus-modified molecular sieve, wherein diammonium hydrogen phosphate, an HZSM-5 molecular sieve and water were mixed and stirred to form a slurry; and the slurry was heated to 100° C. and maintained for 2 hours, to produce a catalytic cracking catalyst sample, which was denoted as CFZY1.2.

The evaluation was performed in the same manner as Example F1.1, and the result was shown in Table 3.

Comparative Example F1

This example was performed in the same manner as Example F1.1, except that the calcining condition included normal pressure (gauge pressure: 0 MPa) and the calcining was performed in the air atmosphere at a temperature of 550° C. in a muffle furnace, to produce a catalytic cracking catalyst comparative sample, which was denoted as DCFZY1.

The evaluation was performed in the same manner as Example F1.1, and the result was shown in Table 3.

Example F2.1

This example was performed in the same manner as Example F1.1, except that 16.2 g of diammonium hydrogen phosphate was dissolved in 120 g of deionized water at 50° C., the mixture was stirred for 0.5 hours to obtain an aqueous solution containing phosphorus; 113 g of an HZSM-5 molecular sieve was added; the modification was performed with the impregnation method at 20° C. for 2 hours; a pressurized hydrothermal calcining treatment was performed at 600° C. for 2 hours in a condition where an external pressure was applied and water was externally added, i.e. under a pressure of 0.5 MPa in a 30% water vapor atmosphere, to produce a catalytic cracking catalyst sample, which was denoted as CFZY2.1.

The evaluation was performed in the same manner as Example F1.1, and the result was shown in Table 3.

Example F2.2

This example was performed in the same manner as Example F2.1, except that diammonium hydrogen phosphate, an HZSM-5 molecular sieve and water were mixed and stirred to form a slurry, and the slurry was heated to 70° C. and maintained for 2 hours, to produce a catalytic cracking catalyst sample, which was denoted as CFZY2.2.

The evaluation was performed in the same manner as Example F1.1, and the result was shown in Table 3.

Comparative Example F2

This example was performed in the same manner as Example F2.1, except that the calcining condition included normal pressure (gauge pressure: 0 MPa) and the calcining was performed in the air atmosphere at a temperature of 550° C. in a muffle furnace, to produce a catalytic cracking catalyst comparative sample, which was denoted as DCFZY2.

The evaluation was performed in the same manner as Example F1.1, and the result was shown in Table 3.

Example F3.1

This example was performed in the same manner as Example F1.1, except that 10.4 g of phosphoric acid was dissolved in 60 g of deionized water at the ordinary temperature, the mixture was stirred for 2 hours to obtain an aqueous solution containing phosphorus; 113 g of an HZSM-5 molecular sieve was added; the modification was performed with the impregnation method at 20° C. for 4 hours; a pressurized hydrothermal calcining treatment was performed at 400° C. for 2 hours in a condition where an external pressure was applied and water was externally added, i.e. under a pressure of 0.3 MPa in a 100% water vapor atmosphere, to produce a catalytic cracking catalyst sample, which was denoted as CFZY3.1.

The evaluation was performed in the same manner as Example F1.1, and the result was shown in Table 3.

Example F3.2

This example was performed in the same manner as Example F3.1, except that an aqueous solution of a phosphorus-containing compound having a temperature of 80° C. and the HZSM-5 molecular sieve heated to 80° C. were contacted and mixed for 4 hours, to produce a catalytic cracking catalyst sample, which was denoted as CFZY3.2.

The evaluation was performed in the same manner as Example F1.1, and the result was shown in Table 3.

Comparative Example F3

This example was performed in the same manner as Example F3.1, except that the calcining condition included normal pressure (gauge pressure: 0 MPa) and the calcining was performed in the air atmosphere at a temperature of 550° C. in a muffle furnace, to produce a catalytic cracking catalyst comparative sample, which was denoted as DCFZY3.

The evaluation was performed in the same manner as Example F1.1, and the result was shown in Table 3.

Example F4.1

This example was performed in the same manner as Example F1.1, except that 8.1 g of diammonium hydrogen phosphate was dissolved in 120 g of deionized water at the ordinary temperature, the mixture was stirred for 0.5 hours to obtain an aqueous solution containing phosphorus; 113 g of an HZSM-5 molecular sieve was added; the modification was performed with the impregnation method at 20° C. for 2 hours; a pressurized hydrothermal calcining treatment was performed at 300° C. for 2 hours in a condition where an external pressure was applied and water was externally added, i.e. under a pressure of 0.4 MPa in a 100% water vapor atmosphere, to produce a catalytic cracking catalyst sample, which was denoted as CFZY4.1.

The evaluation was performed in the same manner as Example F1.1, and the result was shown in Table 3.

Example F4.2

This example was performed in the same manner as Example F4.1, except that ammonium dihydrogen phosphate, an HZSM-5 molecular sieve and water were mixed and stirred to form a slurry, and the slurry was heated to 90° C. and maintained for 2 hours, to produce a catalytic cracking catalyst sample, which was denoted as CFZY4.2.

The evaluation was performed in the same manner as Example F1.1, and the result was shown in Table 3.

Comparative Example F4

This example was performed in the same manner as Example F4.1, except that the calcining condition included normal pressure (gauge pressure: 0 MPa) and the calcining was performed in the air atmosphere at a temperature of 550° C. in a muffle furnace, to produce a catalytic cracking catalyst comparative sample, which was denoted as DCFZY4.

The evaluation was performed in the same manner as Example F1.1, and the result was shown in Table 3.

Example F5.1

This example was performed in the same manner as Example F1.1, except that 8.5 g of trimethyl phosphate was dissolved in 80 g of deionized water at 90° C., the mixture was stirred for 1 hour to obtain an aqueous solution containing phosphorus; 113 g of an HZSM-5 molecular sieve was added; the modification was performed with the impregnation method at 20° C. for 8 hours; a pressurized hydrothermal calcining treatment was performed at 500° C. for 4 hours in a condition where an external pressure was applied and water was externally added, i.e. at a pressure of 0.8 MPa under a 80% water vapor atmosphere, to produce a catalytic cracking catalyst sample, which was denoted as CFZY5.1.

The evaluation was performed in the same manner as Example F1.1, and the result was shown in Table 3.

Example F5.2

This example was performed in the same manner as Example F5.1, except that trimethyl phosphate, an HZSM-5 molecular sieve and water were mixed and stirred to form a slurry, and the slurry was heated to 120° C. and maintained for 8 hours, to produce a catalytic cracking catalyst sample, which was denoted as CFZY5.2.

The evaluation was performed in the same manner as Example F1.1, and the result was shown in Table 3.

Comparative Example F5

This example was performed in the same manner as Example F5.1, except that the calcining condition included normal pressure (gauge pressure: 0 MPa) and the calcining was performed in the air atmosphere at a temperature of 550° C. in a muffle furnace, to produce a catalytic cracking catalyst comparative sample, which was denoted as DCFZY5.

The evaluation was performed in the same manner as Example F1.1, and the result was shown in Table 3.

Example F6.1

This example was performed in the same manner as Example F1.1, except that 11.6 g of boron phosphate was dissolved in 100 g of deionized water at 100° C., the mixture was stirred for 3 hours to obtain an aqueous solution containing phosphorus; 113 g of an HZSM-5 molecular sieve was added; the modification was performed with the impregnation method at 20° C. for 2 hours; a pressurized hydrothermal calcining treatment was performed at 400° C. for 4 hours in a condition where an external pressure was applied and water was externally added, i.e. at a pressure of 0.3 MPa under a 100% water vapor atmosphere, to produce a catalytic cracking catalyst sample, which was denoted as CFZY6.1.

The evaluation was performed in the same manner as Example F1.1, and the result was shown in Table 3.

Example F6.2

This example was performed in the same manner as Example F6.1, except that boron phosphate, an HZSM-5 molecular sieve and water were mixed and stirred to form a slurry, and the slurry was heated to 150° C. and maintained for 2 hours, to produce a catalytic cracking catalyst sample, which was denoted as CFZY6.2.

The evaluation was performed in the same manner as Example F1.1, and the result was shown in Table 3.

Comparative Example F6

This example was performed in the same manner as Example F6.1, except that the calcining condition included normal pressure (gauge pressure: 0 MPa) and the calcining was performed in the air atmosphere at a temperature of 550° C. in a muffle furnace, to produce a catalytic cracking catalyst comparative sample, which was denoted as DCFZY6.

The evaluation was performed in the same manner as Example F1.1, and the result was shown in Table 3.

Example F7.1

This example was performed in the same manner as Example F1.1, except that 14.2 g of triphenylphosphine was dissolved in 80 g of deionized water at 100° C., the mixture was stirred for 2 hours to obtain an aqueous solution containing phosphorus; 113 g of an HZSM-5 molecular sieve was added; the modification was performed with the impregnation method at 20° C. for 4 hours; a pressurized hydrothermal calcining treatment was performed at 600° C. for 2 hours in a condition where an external pressure was applied and water was externally added, i.e. at a pressure of 1 MPa under a 30% water vapor atmosphere, to produce a catalytic cracking catalyst sample, which was denoted as CFZY7.1.

The evaluation was performed in the same manner as Example F1.1, and the result was shown in Table 3.

Example F7.2

This example was performed in the same manner as Example F7.1, except that boron phosphate, an HZSM-5 molecular sieve and water were mixed and stirred to form a slurry, and the slurry was heated to 150° C. and maintained for 2 hours, to produce a catalytic cracking catalyst sample, which was denoted as CFZY7.2.

The evaluation was performed in the same manner as Example F1.1, and the result was shown in Table 3.

Comparative Example F7

This example was performed in the same manner as Example F7.1, except that the calcining condition included normal pressure (gauge pressure: 0 MPa) and the calcining was performed in the air atmosphere at a temperature of 550° C. in a muffle furnace, to produce a catalytic cracking catalyst comparative sample, which was denoted as DCFZY7.

The evaluation was performed in the same manner as Example F1.1, and the result was shown in Table 3.

Comparative Example F8

Comparative Example F8 illustrated the current industry-conventional method and the obtained phosphorus-containing modified ZSM-5 comparative sample.

This example was performed in the same manner as Example F1.2, except that 16.2 g of diammonium hydrogen phosphate was dissolved in 60 g of deionized water, and the mixture was stirred for 0.5 hours to obtain an aqueous solution containing phosphorus; 113 g of HZSM-5 molecular sieve was added to the solution and modified by impregnation, i.e., impregnated at 100° C. for 2 hours; the resulting mixture was dried in an oven at 110° C. and then calcined under the normal pressure (gauge pressure: 0 MPa) in the air atmosphere at a temperature of 550° C. in a muffle furnace to produce a phosphorus-modified ZSM-5 molecular sieve sample; said sample was mixed with kaolin and pseudo-boehmite; decationized water and alumina sol were added and the resulting mixture was stirred for 120 minutes to obtain a slurry with a solid content of 30 wt %; hydrochloric acid was added to adjust the pH value of the slurry to 3.0; then the mixture continued to be stirred for 45 minutes; then the phosphorus-aluminum inorganic binder, Binder 1, was added, and the resulting mixture was stirred for 30 minutes; the resulting slurry was shaped by spray-drying to produce microspheres (having a diameter of 1-150 m); the microspheres were calcined at 500° C. for 1 hour to produce a catalytic cracking catalyst comparative sample, which was denoted as DCFZY8.

The evaluation was performed in the same manner as Example F1.1, and the result was shown in Table 3.

Example F8.1

This example was performed in the same manner as Example F1.1, except that the phosphorus-aluminum inorganic binder was replaced with Binder 2, to produce a catalytic cracking catalyst, which was denoted as CFZY8.1.

The evaluation was performed in the same manner as Example F1.1, and the result was shown in Table 3.

Example F8.2

This example was performed in the same manner as Example F1.2, except that the phosphorus-aluminum inorganic binder was replaced with Binder 2, to produce a catalytic cracking catalyst, which was denoted as CFZY8.2.

The evaluation was performed in the same manner as Example F1.1, and the result was shown in Table 3.

Example F9.1

This example was performed in the same manner as Example F5.1, except that the phosphorus-aluminum inorganic binder was replaced with Binder 3, to produce a catalytic cracking catalyst, which was denoted as CFZY9.1.

The evaluation was performed in the same manner as Example F1.1, and the result was shown in Table 3.

Example F9.2

This example was performed in the same manner as Example F1.2, except that the phosphorus-aluminum inorganic binder was replaced with Binder 3, to produce a catalytic cracking catalyst, which was denoted as CFZY9.2.

The evaluation was performed in the same manner as Example F1.1, and the result was shown in Table 3.

Example F10.1

This example was performed in the same manner as Example F1.1, except that the phosphorus-aluminum inorganic binder was replaced with Binder 4, to produce a catalytic cracking catalyst, which was denoted as CFZY10.1.

The evaluation was performed in the same manner as Example F1.1, and the result was shown in Table 3.

Example F10.2

This example was performed in the same manner as Example F1.2, except that the phosphorus-aluminum inorganic binder was replaced with Binder 4, to produce a catalytic cracking catalyst, which was denoted as CFZY10.2.

The evaluation was performed in the same manner as Example F1.1, and the result was shown in Table 3.

Example F11.X to Example F20.X illustrated the preparation of the catalytic cracking catalysts with the phosphorus-modified hierarchical ZSM-5 molecular sieves according to the present invention.

Example F11.1 to Example F17.1

Example F11.1 to Example F17.1 corresponded to Example F1.1 to Example F7.1 in sequence respectively, except that the HZSM-5 molecular sieve was replaced with a hierarchical ZSM-5 molecular sieve (provided by Changling Division of Sinopec Catalyst Company, and having a relative crystallinity of 88.6%, a silica/alumina molar ratio of 20.8, a $Na_2O$ content of 0.017 wt %, a specific surface area of 373 $m^2/g$, a total pore volume of 0.256 mL/g, a mesoporous volume of 0.119 ml/g, and an average pore size of 5.8 nm, the same below), to produce catalytic cracking catalyst samples, which were denoted as CFZY11.1 to CFZY17.1.

The evaluation was performed in the same manner as Example F1.1, and the result was shown in Table 3.

Example F11.2 to Example F17.2

Example F11.2 to Example F17.2 corresponded to Example F1.2 to Example F7.2 in sequence respectively, except that the HZSM-5 molecular sieve was replaced with a hierarchical ZSM-5 molecular sieve, to produce catalytic cracking catalyst samples, which were denoted as CFZY11.2 to CFZY17.2.

The evaluation was performed in the same manner as Example F1.1, and the result was shown in Table 3.

Comparative Example F9 to Comparative Example F15

Comparative Example F9 to Comparative Example F15 corresponded to Comparative Example F1 to Comparative Example F7 in sequence respectively, except that the HZSM-5 molecular sieve was replaced with a hierarchical ZSM-5 molecular sieve, to produce catalytic cracking catalyst samples, which were denoted as DCFZY9 to DCFZY15.

The evaluation was performed in the same manner as Example F1.1, and the result was shown in Table 3.

Comparative Example F16

Comparative Example F16 illustrated the current industry-conventional method and the obtained phosphorus-containing modified hierarchical ZSM-5 comparative sample. This example was performed in the same manner as Comparative Example F8, except that the HZSM-5 molecular sieve was replaced with a hierarchical ZSM-5 molecular sieve, to produce a catalytic cracking catalyst comparative sample, which was denoted as DCFZY16.

The evaluation was performed in the same manner as Example F1.1, and the result was shown in Table 3.

Example F18.1

This example was performed in the same manner as Example F11.1, except that the phosphorus-aluminum inorganic binder was replaced with Binder 2, to produce a catalytic cracking catalyst, which was denoted as CFZY18.1.

The evaluation was performed in the same manner as Example F1.1, and the result was shown in Table 3.

Example F18.2

This example was performed in the same manner as Example F11.2, except that the phosphorus-aluminum inorganic binder was replaced with Binder 2, to produce a catalytic cracking catalyst, which was denoted as CFZY18.2.

The evaluation was performed in the same manner as Example F1.1, and the result was shown in Table 3.

Example F19.1

This example was performed in the same manner as Example F11.1, except that the phosphorus-aluminum inorganic binder was replaced with Binder 3, to produce a catalytic cracking catalyst, which was denoted as CFZY19.1.

The evaluation was performed in the same manner as Example F1.1, and the result was shown in Table 3.

Example F19.2

This example was performed in the same manner as Example F11.2, except that the phosphorus-aluminum inorganic binder was replaced with Binder 3, to produce a catalytic cracking catalyst, which was denoted as CFZY19.2.

The evaluation was performed in the same manner as Example F1.1, and the result was shown in Table 3.

Example F20.1

This example was performed in the same manner as Example F11.1, except that the phosphorus-aluminum inorganic binder was replaced with Binder 4, to produce a catalytic cracking catalyst, which was denoted as CFZY20.1.

The evaluation was performed in the same manner as Example F1.1, and the result was shown in Table 3.

Example F20.2

This example was performed in the same manner as Example F11.2, except that the phosphorus-aluminum inorganic binder was replaced with Binder 4, to produce a catalytic cracking catalyst, which was denoted as CFZY20.2.

The evaluation was performed in the same manner as Example F1.1, and the result was shown in Table 3.

In Example F21.1, Example F22.1 and Comparative Example F17, another Y-type molecular sieve, HRY-1 commercial molecular sieve, was used.

Example F21.1

This example was performed in the same manner as Example F1.1, except that the Y-type molecular sieve (PSRY) was replaced with HRY-1, to produce a catalyst sample, which was denoted as CFZY21.1.

The evaluation was performed in the same manner as Example F1.1, and the result was shown in Table 3.

Example F22.1

This example was performed in the same manner as Example F11.1, except that the Y-type molecular sieve (PSRY) was replaced with HRY-1, to produce a catalyst sample, which was denoted as CFZY22.1.

The evaluation was performed in the same manner as Example F1.1, and the result was shown in Table 3.

Comparative Example F17

This example was performed in the same manner as Example F1.1, except that the Y-type molecular sieve (PSRY) was replaced with HRY-1, to produce a catalyst sample, which was denoted as DCFZY17.

The evaluation was performed in the same manner as Example F1.1, and the result was shown in Table 3.

In Example F23.1 and Example F24.1, the addition amounts of pseudo-boehmite and alumina sol were increased to replace the phosphorus-aluminum inorganic binder.

Example F23.1

This example was performed in the same manner as Example F1.1, except that the addition amounts of pseudo-boehmite and alumina sol were increased to replace the phosphorus-aluminum inorganic binder, Binder 1, to produce a catalytic cracking auxiliary sample, which was denoted as CFZY23.1.

The evaluation was performed in the same manner as Example F1.1, and the result was shown in Table 3.

Example F24.1

This example was performed in the same manner as Example F11.1, except that the addition amounts of pseudo-boehmite and alumina sol were increased to replace the phosphorus-aluminum inorganic binder, Binder 1, to produce a catalytic cracking auxiliary sample, which was denoted as CFZY24.1.

The evaluation was performed in the same manner as Example F1.1, and the result was shown in Table

TABLE 3

| Example/ Comparative Example | D-value of Catalytic Cracking Catalyst | Catalyst Mixture | | Material Balance, wt % | | |
|---|---|---|---|---|---|---|
| | | | | Liquefied Gas | Ethylene Yield | Propylene Yield |
| Blank | / | / | 100% equilibrium catalyst | 18.54 | 1.39 | 8.05 |
| F1.1 | 69% | 10% CFZY1.1 | 90% equilibrium catalyst | 39.28 | 4.17 | 19.51 |
| F1.2 | 74% | 10% CFZY1.2 | 90% equilibrium catalyst | 46.92 | 5.09 | 21.68 |

TABLE 3-continued

| Example/ Comparative Example | D-value of Catalytic Cracking Catalyst | Catalyst Mixture | | Material Balance, wt % | | |
|---|---|---|---|---|---|---|
| | | | | Liquefied Gas | Ethylene Yield | Propylene Yield |
| F2.1 | 73% | 10% CFZY2.1 | 90% equilibrium catalyst | 47.58 | 4.87 | 20.40 |
| F2.2 | 75% | 10% CFZY2.2 | 90% equilibrium catalyst | 52.40 | 5.42 | 21.27 |
| F3.1 | 70% | 10% CFZY3.1 | 90% equilibrium catalyst | 44.24 | 4.63 | 18.39 |
| F3.2 | 74% | 10% CFZY3.2 | 90% equilibrium catalyst | 48.15 | 5.09 | 19.82 |
| F4.1 | 72% | 10% CFZY4.1 | 90% equilibrium catalyst | 46.45 | 4.69 | 19.09 |
| F4.2 | 74% | 10% CFZY4.2 | 90% equilibrium catalyst | 50.57 | 5.21 | 20.11 |
| F5.1 | 67% | 10% CFZY5.1 | 90% equilibrium catalyst | 40.52 | 4.17 | 16.56 |
| F5.2 | 72% | 10% CFZY5.2 | 90% equilibrium catalyst | 44.25 | 4.54 | 18.39 |
| F6.1 | 73% | 10% CFZY6.1 | 90% equilibrium catalyst | 45.74 | 4.41 | 18.72 |
| F6.2 | 75% | 10% CFZY6.2 | 90% equilibrium catalyst | 50.51 | 5.21 | 19.86 |
| F7.1 | 66% | 10% CFZY7.1 | 90% equilibrium catalyst | 33.34 | 3.34 | 13.60 |
| F7.2 | 67% | 10% CFZY7.2 | 90% equilibrium catalyst | 38.72 | 4.17 | 16.52 |
| F8.1 | 66% | 10% CFZY8.1 | 90% equilibrium catalyst | 37.05 | 4.00 | 19.13 |
| F8.2 | 72% | 10% CFZY8.2 | 90% equilibrium catalyst | 46.06 | 4.41 | 20.32 |
| F9.1 | 67% | 10% CFZY9.1 | 90% equilibrium catalyst | 36.54 | 3.94 | 19.08 |
| F9.2 | 73% | 10% CFZY9.2 | 90% equilibrium catalyst | 45.21 | 4.17 | 19.79 |
| F10.1 | 68% | 10% CFZY10.1 | 90% equilibrium catalyst | 36.65 | 3.83 | 18.70 |
| F10.2 | 71% | 10% CFZY10.2 | 90% equilibrium catalyst | 45.38 | 4.19 | 19.77 |
| F11.1 | 68% | 10% CFZY11.1 | 90% equilibrium catalyst | 40.86 | 4.25 | 20.29 |
| F11.2 | 75% | 10% CFZY11.2 | 90% equilibrium catalyst | 48.80 | 5.19 | 22.55 |
| F12.1 | 75% | 10% CFZY12.1 | 90% equilibrium catalyst | 49.48 | 4.97 | 21.22 |
| F12.2 | 78% | 10% CFZY12.2 | 90% equilibrium catalyst | 54.50 | 5.53 | 22.12 |
| F13.1 | 71% | 10% CFZY13.1 | 90% equilibrium catalyst | 46.01 | 4.72 | 19.13 |
| F13.2 | 72% | 10% CFZY13.2 | 90% equilibrium catalyst | 50.07 | 5.19 | 20.61 |
| F14.1 | 73% | 10% CFZY14.1 | 90% equilibrium catalyst | 48.31 | 4.78 | 19.85 |
| F14.2 | 76% | 10% CFZY14.2 | 90% equilibrium catalyst | 52.59 | 5.31 | 20.91 |
| F15.1 | 70% | 10% CFZY15.1 | 90% equilibrium catalyst | 42.14 | 4.25 | 17.22 |
| F15.2 | 74% | 10% CFZY15.2 | 90% equilibrium catalyst | 46.02 | 4.63 | 19.13 |
| F16.1 | 70% | 10% CFZY16.1 | 90% equilibrium catalyst | 47.57 | 4.50 | 19.47 |
| F16.2 | 74% | 10% CFZY16.2 | 90% equilibrium catalyst | 52.52 | 5.31 | 20.65 |
| F17.1 | 66% | 10% CFZY17.1 | 90% equilibrium catalyst | 34.67 | 3.41 | 14.14 |
| F17.2 | 70% | 10% CFZY17.2 | 90% equilibrium catalyst | 40.28 | 4.25 | 17.18 |
| F18.1 | 66% | 10% CFZY18.1 | 90% equilibrium catalyst | 38.54 | 4.08 | 19.90 |
| F18.2 | 75% | 10% CFZY18.2 | 90% equilibrium catalyst | 47.90 | 4.50 | 21.13 |
| F19.1 | 66% | 10% CFZY19.1 | 90% equilibrium catalyst | 38.00 | 4.02 | 19.84 |
| F19.2 | 72% | 10% CFZY19.2 | 90% equilibrium catalyst | 47.02 | 4.25 | 20.58 |
| F20.1 | 66% | 10% CFZY20.1 | 90% equilibrium catalyst | 38.12 | 3.91 | 19.45 |

TABLE 3-continued

| Example/ Comparative Example | D-value of Catalytic Cracking Catalyst | Catalyst Mixture | Material Balance, wt % | | |
|---|---|---|---|---|---|
| | | | Liquefied Gas | Ethylene Yield | Propylene Yield |
| F20.2 | 73% | 10% CFZY20.2 | 90% equilibrium catalyst | 47.20 | 4.27 | 20.56 |
| F21.1 | 65% | 10% CFZY21.1 | 90% equilibrium catalyst | 37.32 | 4.00 | 18.34 |
| F22.1 | 71% | 10% CFZY22.1 | 90% equilibrium catalyst | 44.57 | 4.89 | 20.38 |
| F23.1 | 66% | 10% CFZY23.1 | 90% equilibrium catalyst | 35.35 | 3.75 | 17.56 |
| F24.1 | 66% | 10% CFZY24.1 | 90% equilibrium catalyst | 36.77 | 3.83 | 18.26 |
| F1 | 59% | 10% DCFZY1 | 90% equilibrium catalyst | 31.74 | 3.10 | 13.99 |
| F2 | 60% | 10% DCFZY2 | 90% equilibrium catalyst | 33.63 | 3.26 | 15.11 |
| F3 | 58% | 10% DCFZY3 | 90% equilibrium catalyst | 31.88 | 3.22 | 14.33 |
| F4 | 61% | 10% DCFZY4 | 90% equilibrium catalyst | 34.05 | 3.40 | 15.57 |
| F5 | 54% | 10% DCFZY5 | 90% equilibrium catalyst | 27.75 | 3.56 | 12.04 |
| F6 | 60% | 10% DCFZY6 | 90% equilibrium catalyst | 34.20 | 3.40 | 16.17 |
| F7 | 48% | 10% DCFZY7 | 90% equilibrium catalyst | 22.75 | 3.50 | 11.06 |
| F8 | 52% | 10% DCFZY8 | 90% equilibrium catalyst | 30.23 | 3.04 | 13.32 |
| F9 | 60% | 10% DCFZY9 | 90% equilibrium catalyst | 33.01 | 3.16 | 14.55 |
| F10 | 58% | 10% DCFZY10 | 90% equilibrium catalyst | 34.98 | 3.33 | 15.71 |
| F11 | 61% | 10% DCFZY11 | 90% equilibrium catalyst | 33.15 | 3.28 | 14.90 |
| F12 | 58% | 10% DCFZY12 | 90% equilibrium catalyst | 35.42 | 3.47 | 16.19 |
| F13 | 52% | 10% DCFZY13 | 90% equilibrium catalyst | 28.86 | 3.63 | 12.52 |
| F14 | 58% | 10% DCFZY14 | 90% equilibrium catalyst | 35.56 | 3.47 | 16.82 |
| F15 | 50% | 10% DCFZY15 | 90% equilibrium catalyst | 23.67 | 3.57 | 11.50 |
| F16 | 51% | 10% DCFZY16 | 90% equilibrium catalyst | 31.44 | 3.10 | 13.85 |
| F17 | 50% | 10% DCFZY17 | 90% equilibrium catalyst | 30.15 | 2.98 | 13.15 |

Example E1.X to Example E22.X provided the catalytic cracking auxiliaries of the present invention, and Comparative Example E1 to Comparative Example E16 illustrated the comparative catalytic cracking auxiliaries. Microporous ZSM-5 molecular sieves were used in Example E1.X to Example E10.X and Example E21.1, and hierarchical ZSM-5 molecular sieves were used in Example E11.X to Example E20.X and Example E22.1. Comparative Example E8 was a comparative catalytic cracking auxiliary containing the micropore ZSM-5 molecular sieve prepared by the prior art, and Comparative Example E16 was a comparative catalytic cracking auxiliary containing the hierarchical ZSM-5 molecular sieve prepared by the prior art.

Example E1.1

16.2 g of diammonium hydrogen phosphate (Tianjin Guangfu Science and Technology Development Co., Ltd., analysis pure, the same below) was dissolved in 60 g of deionized water, and the mixture was stirred for 0.5 hours to obtain an aqueous solution containing phosphorus; 113 g of HZSM-5 molecular sieve (provided by Changling Division of Sinopec Catalyst Company and having a relative crystallinity of 91.1%, a silica/alumina molar ratio of 24.1, a $Na_2O$ content of 0.039 wt %, a specific surface area of 353 m²/g, and a total pore volume of 0.177 mL/g, the same below) was added to the solution and modified by impregnation, i.e., impregnated at 20° C. for 2 hours; the resulting mixture was mixed with kaolin and pseudo-boehmite; decationized water and alumina sol were added and the resulting mixture was stirred for 120 minutes to obtain a slurry with a solid content of 30 wt %; hydrochloric acid was added to adjust the pH value of the slurry to 3.0; then the mixture continued to be stirred for 45 minutes; then the phosphorus-aluminum inorganic binder, Binder 1, was added, and the resulting mixture was stirred for 30 minutes; the resulting slurry was shaped by spray-drying to produce microspheres (having a diameter of 1-150 m); the microspheres were treated at 500° C. for 0.5 hours in a condition where an external pressure was applied and water was externally added, i.e. under a pressure of 0.5 MPa in a 50% water vapor atmosphere to produce a catalytic cracking auxiliary sample, which was denoted as CEZ1.1, the composition of which comprised 50% of the molecular sieve, 23% of kaolin, 18% of Binder 1, 5% of pseudo-boehmite (as $Al_2O_3$), and 4% of alumina sol (as $Al_2O_3$).

A fixed bed micro-reaction apparatus was used to evaluate the reaction performances of a 100% equilibrium catalyst and an equilibrium catalyst to which the catalytic cracking auxiliary CEZ1.1 prepared in Example E1.1 was incorporated, in order to illustrate the catalytic cracking reaction effect of the catalytic cracking auxiliary provided in the present disclosure.

The auxiliary CEZ1.1 was aged at 800° C. in a 100% water vapor atmosphere for 17 hours. The aged CEZ1.1 was mixed with an industrial FCC equilibrium catalyst (an FCC equilibrium catalyst with the industry brand of DVR-3 having a light oil micro-activity of 63). A mixture of the equilibrium catalyst and the auxiliary was loaded into the fixed-bed micro-reaction reactor, and the feedstock oil shown in Table 2 was catalytically cracked. The evaluation condition included the reaction temperature of 620° C., the regeneration temperature of 620° C., and the catalyst-oil ratio was 3.2. Table 4 provided the reaction results, including the blank test agent.

Example E1.2

This example was performed in the same manner as Example E1.1, except for the preparation of the phosphorus-modified molecular sieve, wherein diammonium hydrogen phosphate, an HZSM-5 molecular sieve and water were mixed and stirred to form a slurry; and the slurry was heated to 100° C. and maintained for 2 hours, to produce a catalytic cracking auxiliary sample, which was denoted as CEZ1.2.

The evaluation was performed in the same manner as Example E1.1, and the result was shown in Table 4.

Comparative Example E1

This example was performed in the same manner as Example E1.1, except that the calcining condition included normal pressure (gauge pressure: 0 MPa) and the calcining was performed in the air atmosphere at a temperature of 550° C. in a muffle furnace, to produce a catalytic cracking auxiliary comparative sample, which was denoted as DCEZ1.

The evaluation was performed in the same manner as Example E1.1, and the result was shown in Table 4.

Example E2.1

This example was performed in the same manner as Example E1.1, except that 16.2 g of diammonium hydrogen phosphate was dissolved in 120 g of deionized water at 50° C., the mixture was stirred for 0.5 hours to obtain an aqueous solution containing phosphorus; 113 g of an HZSM-5 molecular sieve was added; the modification was performed with the impregnation method at 20° C. for 2 hours; a pressurized hydrothermal calcining treatment was performed at 600° C. for 2 hours in a condition where an external pressure was applied and water was externally added, i.e. at a pressure of 0.5 MPa under a 30% water vapor atmosphere, to produce a catalytic cracking auxiliary sample, which was denoted as CEZ2.1.

The evaluation was performed in the same manner as Example E1.1, and the result was shown in Table 4.

Example E2.2

This example was performed in the same manner as Example E2.1, except that diammonium hydrogen phosphate, an HZSM-5 molecular sieve and water were mixed and stirred to form a slurry, and the slurry was heated to 70° C. and maintained for 2 hours, to produce a catalytic cracking auxiliary sample, which was denoted as CEZ2.2.

The evaluation was performed in the same manner as Example E1.1, and the result was shown in Table 4.

Comparative Example E2

This example was performed in the same manner as Example E2.1, except that the calcining condition included normal pressure (gauge pressure: 0 MPa) and the calcining was performed in the air atmosphere at a temperature of 550° C. in a muffle furnace, to produce a catalytic cracking auxiliary comparative sample, which was denoted as DCEZ2.

The evaluation was performed in the same manner as Example E1.1, and the result was shown in Table 4.

Example E3.1

This example was performed in the same manner as Example E1.1, except that 10.4 g of phosphoric acid was dissolved in 60 g of deionized water at the ordinary temperature, the mixture was stirred for 2 hours to obtain an aqueous solution containing phosphorus; 113 g of an HZSM-5 molecular sieve was added; the modification was performed with the impregnation method at 20° C. for 4 hours; a pressurized hydrothermal calcining treatment was performed at 400° C. for 2 hours in a condition where an external pressure was applied and water was externally added, i.e. under a pressure of 0.3 MPa in a 100% water vapor atmosphere, to produce a catalytic cracking auxiliary sample, which was denoted as CEZ3.1.

The evaluation was performed in the same manner as Example E1.1, and the result was shown in Table 4.

Example E3.2

This example was performed in the same manner as Example E3.1, except that an aqueous solution of a phosphorus-containing compound having a temperature of 80° C. and the HZSM-5 molecular sieve heated to 80° C. were contacted and mixed for 4 hours, to produce a catalytic cracking auxiliary sample, which was denoted as CEZ3.2.

The evaluation was performed in the same manner as Example E1.1, and the result was shown in Table 4.

Comparative Example E3

This example was performed in the same manner as Example E3.1, except that the calcining condition included normal pressure (gauge pressure: 0 MPa) and the calcining was performed in the air atmosphere at a temperature of 550° C. in a muffle furnace, to produce a catalytic cracking auxiliary comparative sample, which was denoted as DCEZ3.

The evaluation was performed in the same manner as Example E1.1, and the result was shown in Table 4.

Example E4.1

This example was performed in the same manner as Example E1.1, except that 8.1 g of diammonium hydrogen phosphate was dissolved in 120 g of deionized water at the ordinary temperature, the mixture was stirred for 0.5 hours to obtain an aqueous solution containing phosphorus; 113 g of an HZSM-5 molecular sieve was added; the modification was performed with the impregnation method at 20° C. for 2 hours; a pressurized hydrothermal calcining treatment was performed at 300° C. for 2 hours in a condition where an external pressure was applied and water was externally added, i.e. at a pressure of 0.4 MPa under a 100% water vapor atmosphere, to produce a catalytic cracking auxiliary sample, which was denoted as CEZ4.1.

The evaluation was performed in the same manner as Example E1.1, and the result was shown in Table 4.

Example E4.2

This example was performed in the same manner as Example E4.1, except that ammonium dihydrogen phosphate, an HZSM-5 molecular sieve and water were mixed and stirred to form a slurry, and the slurry was heated to 90° C. and maintained for 2 hours, to produce a catalytic cracking auxiliary sample, which was denoted as CEZ4.2.

The evaluation was performed in the same manner as Example E1.1, and the result was shown in Table 4.

Comparative Example E4

This example was performed in the same manner as Example E4.1, except that the calcining condition included normal pressure (gauge pressure: 0 MPa) and the calcining was performed in the air atmosphere at a temperature of 550° C. in a muffle furnace, to produce a catalytic cracking auxiliary comparative sample, which was denoted as DCEZ4.

The evaluation was performed in the same manner as Example E1.1, and the result was shown in Table 4.

Example E5.1

This example was performed in the same manner as Example E1.1, except that 8.5 g of trimethyl phosphate was dissolved in 80 g of deionized water at 90° C., the mixture was stirred for 1 hour to obtain an aqueous solution containing phosphorus; 113 g of an HZSM-5 molecular sieve was added; the modification was performed with the impregnation method at 20° C. for 8 hours; a pressurized hydrothermal calcining treatment was performed at 500° C. for 4 hours in a condition where an external pressure was applied and water was externally added, i.e. at a pressure of 0.8 MPa under a 80% water vapor atmosphere, to produce a catalytic cracking auxiliary sample, which was denoted as CEZ5.1.

The evaluation was performed in the same manner as Example E1.1, and the result was shown in Table 4.

Example E5.2

This example was performed in the same manner as Example E5.1, except that trimethyl phosphate, an HZSM-5 molecular sieve and water were mixed and stirred to form a slurry, and the slurry was heated to 120° C. and maintained for 8 hours, to produce a catalytic cracking auxiliary sample, which was denoted as CEZ5.2.

The evaluation was performed in the same manner as Example E1.1, and the result was shown in Table 4.

Comparative Example E5

This example was performed in the same manner as Example E5.1, except that the calcining condition included normal pressure (gauge pressure: 0 MPa) and the calcining was performed in the air atmosphere at a temperature of 550° C. in a muffle furnace, to produce a catalytic cracking auxiliary comparative sample, which was denoted as DCEZ5.

The evaluation was performed in the same manner as Example E1.1, and the result was shown in Table 4.

Example E6.1

This example was performed in the same manner as Example E1.1, except that 11.6 g of boron phosphate was dissolved in 100 g of deionized water at 100° C., the mixture was stirred for 3 hours to obtain an aqueous solution containing phosphorus; 113 g of an HZSM-5 molecular sieve was added; the modification was performed with the impregnation method at 20° C. for 2 hours; a pressurized hydrothermal calcining treatment was performed at 400° C. for 4 hours in a condition where an external pressure was applied and water was externally added, i.e. at a pressure of 0.3 MPa under a 100% water vapor atmosphere, to produce a catalytic cracking auxiliary sample, which was denoted as CEZ6.1.

The evaluation was performed in the same manner as Example E1.1, and the result was shown in Table 4.

Example E6.2

This example was performed in the same manner as Example E6.1, except that boron phosphate, an HZSM-5 molecular sieve and water were mixed and stirred to form a slurry, and the slurry was heated to 150° C. and maintained for 2 hours, to produce a catalytic cracking auxiliary sample, which was denoted as CEZ6.2.

The evaluation was performed in the same manner as Example E1.1, and the result was shown in Table 4.

Comparative Example E6

This example was performed in the same manner as Example E6.1, except that the calcining condition included normal pressure (gauge pressure: 0 MPa) and the calcining was performed in the air atmosphere at a temperature of 550° C. in a muffle furnace, to produce a catalytic cracking auxiliary comparative sample, which was denoted as DCEZ6.

The evaluation was performed in the same manner as Example E1.1, and the result was shown in Table 4.

Example E7.1

This example was performed in the same manner as Example E1.1, except that 14.2 g of triphenylphosphine was dissolved in 80 g of deionized water at 100° C., the mixture was stirred for 2 hours to obtain an aqueous solution containing phosphorus; 113 g of an HZSM-5 molecular sieve was added; the modification was performed with the impregnation method at 20° C. for 4 hours; a pressurized hydrothermal calcining treatment was performed at 600° C. for 2 hours in a condition where an external pressure was applied and water was externally added, i.e. at a pressure of 1 MPa under a 30% water vapor atmosphere, to produce a catalytic cracking auxiliary sample, which was denoted as CEZ7.1.

The evaluation was performed in the same manner as Example E1.1, and the result was shown in Table 4.

Example E7.2

This example was performed in the same manner as Example E7.1, except that boron phosphate, an HZSM-5 molecular sieve and water were mixed and stirred to form a slurry, and the slurry was heated to 150° C. and maintained for 2 hours, to produce a catalytic cracking auxiliary sample, which was denoted as CEZ7.2.

The evaluation was performed in the same manner as Example E1.1, and the result was shown in Table 4.

Comparative Example E7

This example was performed in the same manner as Example E7.1, except that the calcining condition included normal pressure (gauge pressure: 0 MPa) and the calcining was performed in the air atmosphere at a temperature of 550° C. in a muffle furnace, to produce a catalytic cracking auxiliary comparative sample, which was denoted as DCEZ7.

The evaluation was performed in the same manner as Example E1.1, and the result was shown in Table 4.

Comparative Example E8

Comparative Example E8 illustrated the current industry-conventional method and the obtained phosphorus-containing modified ZSM-5 comparative sample.

This example was performed in the same manner as Example E1.2, except that 16.2 g of diammonium hydrogen phosphate was dissolved in 60 g of deionized water, and the mixture was stirred for 0.5 hours to obtain an aqueous solution containing phosphorus; 113 g of HZSM-5 molecular sieve was added to the solution and modified by impregnation, i.e., impregnated at 100° C. for 2 hours; the resulting mixture was dried in an oven at 110° C. and then calcined under the normal pressure (gauge pressure: 0 MPa) in the air atmosphere at a temperature of 550° C. in a muffle furnace to produce a phosphorus-modified ZSM-5 molecular sieve sample; said sample was mixed with kaolin and pseudo-boehmite; decationized water and alumina sol were added and the resulting mixture was stirred for 120 minutes to obtain a slurry with a solid content of 30 wt %; hydrochloric acid was added to adjust the pH value of the slurry to 3.0; then the mixture continued to be stirred for 45 minutes; then the phosphorus-aluminum inorganic binder, Binder 1, was added, and the resulting mixture was stirred for 30 minutes; the resulting slurry was shaped by spray-drying to produce microspheres (having a diameter of 1-150 m); the microspheres were calcined at 500° C. for 1 hour to produce a catalytic cracking auxiliary comparative sample, which was denoted as DCEZ8.

The evaluation was performed in the same manner as Example E1.1, and the result was shown in Table 4.

Example E8.1

This example was performed in the same manner as Example E1.1, except that the phosphorus-aluminum inorganic binder was replaced with Binder 2, to produce a catalytic cracking auxiliary, which was denoted as CEZ8.1.

The evaluation was performed in the same manner as Example E1.1, and the result was shown in Table 4.

Example E8.2

This example was performed in the same manner as Example E1.2, except that the phosphorus-aluminum inorganic binder was replaced with Binder 2, to produce a catalytic cracking auxiliary, which was denoted as CEZ8.2.

The evaluation was performed in the same manner as Example E1.1, and the result was shown in Table 4.

Example E9.1

This example was performed in the same manner as Example E1.1, except that the phosphorus-aluminum inorganic binder was replaced with Binder 3, to produce a catalytic cracking auxiliary, which was denoted as CEZ9.1.

The evaluation was performed in the same manner as Example E1.1, and the result was shown in Table 4.

Example E9.2

This example was performed in the same manner as Example E1.2, except that the phosphorus-aluminum inorganic binder was replaced with Binder 3, to produce a catalytic cracking auxiliary, which was denoted as CEZ9.2.

The evaluation was performed in the same manner as Example E1.1, and the result was shown in Table 4.

Example E10.1

This example was performed in the same manner as Example E1.1, except that the phosphorus-aluminum inorganic binder was replaced with Binder 4, to produce a catalytic cracking auxiliary, which was denoted as CEZ10.1. The evaluation was performed in the same manner as Example E5.1, and the result was shown in Table 4.

Example E10.2

This example was performed in the same manner as Example E1.2, except that the phosphorus-aluminum inorganic binder was replaced with Binder 4, to produce a catalytic cracking auxiliary, which was denoted as CEZ10.2.

The evaluation was performed in the same manner as Example E1.1, and the result was shown in Table 4.

Example E11.X to Example E20.X illustrated the preparation of the catalytic cracking auxiliary with the phosphorus-modified hierarchical ZSM-5 molecular sieves according to the present invention.

Example E11.1 to Example E17.1

Example E11.1 to Example E17.1 corresponded to Example E1.1 to Example E7.1 in sequence respectively, except that the HZSM-5 molecular sieve was replaced with a hierarchical ZSM-5 molecular sieve (provided by Changling Division of Sinopec Catalyst Company, and having a relative crystallinity of 88.6%, a silica/alumina molar ratio of 20.8, a $Na_2O$ content of 0.017 wt %, a specific surface area of 373 $m^2/g$, a total pore volume of 0.256 mL/g, a mesoporous volume of 0.119 ml/g, and an average pore size of 5.8 nm, the same below), to produce catalytic cracking auxiliary samples, which were denoted as CEZ11.1 to CEZ17.1. The evaluation was performed in the same manner as Example E1.1, and the result was shown in Table 4.

Example E11.2 to Example E17.2

Example E11.2 to Example E17.2 corresponded to Example E1.2 to Example E7.2 in sequence respectively, except that the HZSM-5 molecular sieve was replaced with a hierarchical ZSM-5 molecular sieve, to produce catalytic cracking auxiliary samples, which were denoted as CEZ11.2 to CEZ17.2.

The evaluation was performed in the same manner as Example E1.1, and the result was shown in Table 4.

Comparative Example E9 to Comparative Example E15

Comparative Example E9 to Comparative Example E15 corresponded to Comparative Example E1 to Comparative Example E7 in sequence respectively, except that the HZSM-5 molecular sieve was replaced with a hierarchical ZSM-5 molecular sieve, to produce catalytic cracking auxiliary samples, which were denoted as DCEZ9 to DCEZ15.

The evaluation was performed in the same manner as Example E1.1, and the result was shown in Table 4.

Comparative Example E16

Comparative Example E16 illustrated the current industry-conventional method and the obtained phosphorus-containing modified hierarchical ZSM-5 comparative sample. This example was performed in the same manner as Comparative Example E8, except that the HZSM-5 molecular sieve was replaced with a hierarchical ZSM-5 molecular sieve, to produce a catalytic cracking auxiliary comparative sample, which was denoted as DCEZ16.

The evaluation was performed in the same manner as Example E1.1, and the result was shown in Table 4.

Example E18.1

This example was performed in the same manner as Example E11.1, except that the phosphorus-aluminum inorganic binder was replaced with Binder 2, to produce a catalytic cracking auxiliary, which was denoted as CEZ18.1.

The evaluation was performed in the same manner as Example E1.1, and the result was shown in Table 4.

Example E18.2

This example was performed in the same manner as Example E11.2, except that the phosphorus-aluminum inorganic binder was replaced with Binder 2, to produce a catalytic cracking auxiliary, which was denoted as CEZ18.2.

The evaluation was performed in the same manner as Example E1.1, and the result was shown in Table 4.

Example E19.1

This example was performed in the same manner as Example E11.1, except that the phosphorus-aluminum inorganic binder was replaced with Binder 3, to produce a catalytic cracking auxiliary, which was denoted as CEZ19.1.

The evaluation was performed in the same manner as Example E1.1, and the result was shown in Table 4.

Example E19.2

This example was performed in the same manner as Example E11.2, except that the phosphorus-aluminum inorganic binder was replaced with Binder 3, to produce a catalytic cracking auxiliary, which was denoted as CEZ19.2.

The evaluation was performed in the same manner as Example E1.1, and the result was shown in Table 4.

Example E20.1

This example was performed in the same manner as Example E11.1, except that the phosphorus-aluminum inorganic binder was replaced with Binder 4, to produce a catalytic cracking auxiliary, which was denoted as CEZ20.1.

The evaluation was performed in the same manner as Example E1.1, and the result was shown in Table 4.

Example E20.2

This example was performed in the same manner as Example E11.2, except that the phosphorus-aluminum inorganic binder was replaced with Binder 4, to produce a catalytic cracking auxiliary, which was denoted as CEZ20.2.

The evaluation was performed in the same manner as Example E1.1, and the result was shown in Table 4.

Example E21.1

This example was performed in the same manner as Example E1.1, except that the addition amounts of pseudo-boehmite and alumina sol were increased to replace the phosphorus-aluminum inorganic binder, Binder 1, to produce a catalytic cracking auxiliary sample, which was denoted as CEZ21.1.

The evaluation was performed in the same manner as Example E1.1, and the result was shown in Table 4.

Example E21.2

This example was performed in the same manner as Example E11.1, except that the addition amounts of pseudo-boehmite and alumina sol were increased to replace the phosphorus-aluminum inorganic binder, Binder 1, to produce a catalytic cracking auxiliary sample, which was denoted as CEZ21.2.

The evaluation was performed in the same manner as Example E1.1, and the result was shown in Table 4.

TABLE 4

| Example/Comparative Example | D value of Catalytic Cracking Auxiliary | Catalyst Mixture | | Material Balance, wt % | | |
|---|---|---|---|---|---|---|
| | | | | Liquefied Gas | Ethylene Yield | Propylene Yield |
| Blank | / | / | 100% equilibrium catalyst | 18.54 | 1.39 | 8.05 |
| E1.1 | 86% | 10% CEZ1.1 | 90% equilibrium catalyst | 37.41 | 4.09 | 18.76 |
| E1.2 | 92% | 10% CEZ1.2 | 90% equilibrium catalyst | 44.69 | 4.99 | 20.85 |

TABLE 4-continued

| Example/ Comparative Example | D value of Catalytic Cracking Auxiliary | Catalyst Mixture | | Material Balance, wt % | | |
|---|---|---|---|---|---|---|
| | | | | Liquefied Gas | Ethylene Yield | Propylene Yield |
| E2.1 | 91% | 10% CEZ2.1 | 90% equilibrium catalyst | 45.31 | 4.77 | 19.62 |
| E2.2 | 94% | 10% CEZ2.2 | 90% equilibrium catalyst | 49.90 | 5.31 | 20.45 |
| E3.1 | 88% | 10% CEZ3.1 | 90% equilibrium catalyst | 42.13 | 4.54 | 17.68 |
| E3.2 | 93% | 10% CEZ3.2 | 90% equilibrium catalyst | 45.86 | 4.99 | 19.06 |
| E4.1 | 90% | 10% CEZ4.1 | 90% equilibrium catalyst | 44.24 | 4.60 | 18.36 |
| E4.2 | 93% | 10% CEZ4.2 | 90% equilibrium catalyst | 48.16 | 5.11 | 19.34 |
| E5.1 | 84% | 10% CEZ5.1 | 90% equilibrium catalyst | 38.59 | 4.09 | 15.92 |
| E5.2 | 90% | 10% CEZ5.2 | 90% equilibrium catalyst | 42.14 | 4.45 | 17.68 |
| E6.1 | 91% | 10% CEZ6.1 | 90% equilibrium catalyst | 43.56 | 4.32 | 18.00 |
| E6.2 | 94% | 10% CEZ6.2 | 90% equilibrium catalyst | 48.10 | 5.11 | 19.10 |
| E7.1 | 82% | 10% CEZ7.1 | 90% equilibrium catalyst | 31.75 | 3.27 | 13.08 |
| E7.2 | 84% | 10% CEZ7.2 | 90% equilibrium catalyst | 36.88 | 4.09 | 15.88 |
| E8.1 | 83% | 10% CEZ8.1 | 90% equilibrium catalyst | 35.29 | 3.92 | 18.39 |
| E8.2 | 90% | 10% CEZ8.2 | 90% equilibrium catalyst | 43.87 | 4.32 | 19.54 |
| E9.1 | 84% | 10% CEZ9.1 | 90% equilibrium catalyst | 34.80 | 3.86 | 18.35 |
| E9.2 | 91% | 10% CEZ9.2 | 90% equilibrium catalyst | 43.06 | 4.09 | 19.03 |
| E10.1 | 85% | 10% CEZ10.1 | 90% equilibrium catalyst | 34.90 | 3.75 | 17.98 |
| E10.2 | 89% | 10% CEZ10.2 | 90% equilibrium catalyst | 43.22 | 4.11 | 19.01 |
| E11.1 | 85% | 10% CEZ11.1 | 90% equilibrium catalyst | 38.91 | 4.17 | 19.51 |
| E11.2 | 94% | 10% CEZ11.2 | 90% equilibrium catalyst | 46.48 | 5.09 | 21.68 |
| E12.1 | 94% | 10% CEZ12.1 | 90% equilibrium catalyst | 47.12 | 4.87 | 20.40 |
| E12.2 | 97% | 10% CEZ12.2 | 90% equilibrium catalyst | 51.90 | 5.42 | 21.27 |
| E13.1 | 89% | 10% CEZ13.1 | 90% equilibrium catalyst | 43.82 | 4.63 | 18.39 |
| E13.2 | 90% | 10% CEZ13.2 | 90% equilibrium catalyst | 47.69 | 5.09 | 19.82 |

TABLE 4-continued

| Example/ Comparative Example | D value of Catalytic Cracking Auxiliary | Catalyst Mixture | | Material Balance, wt % | | |
|---|---|---|---|---|---|---|
| | | | | Liquefied Gas | Ethylene Yield | Propylene Yield |
| E14.1 | 91% | 10% CEZ14.1 | 90% equilibrium catalyst | 46.01 | 4.69 | 19.09 |
| E14.2 | 95% | 10% CEZ14.2 | 90% equilibrium catalyst | 50.09 | 5.21 | 20.11 |
| E15.1 | 87% | 10% CEZ15.1 | 90% equilibrium catalyst | 40.13 | 4.17 | 16.56 |
| E15.2 | 92% | 10% CEZ15.2 | 90% equilibrium catalyst | 43.83 | 4.54 | 18.39 |
| E16.1 | 88% | 10% CEZ16.1 | 90% equilibrium catalyst | 45.30 | 4.41 | 18.72 |
| E16.2 | 93% | 10% CEZ16.2 | 90% equilibrium catalyst | 50.02 | 5.21 | 19.86 |
| E17.1 | 83% | 10% CEZ17.1 | 90% equilibrium catalyst | 33.02 | 3.34 | 13.60 |
| E17.2 | 88% | 10% CEZ17.2 | 90% equilibrium catalyst | 38.36 | 4.17 | 16.52 |
| E18.1 | 83% | 10% CEZ18.1 | 90% equilibrium catalyst | 36.70 | 4.00 | 19.13 |
| E18.2 | 94% | 10% CEZ18.2 | 90% equilibrium catalyst | 45.62 | 4.41 | 20.32 |
| E19.1 | 83% | 10% CEZ19.1 | 90% equilibrium catalyst | 36.19 | 3.94 | 19.08 |
| E19.2 | 90% | 10% CEZ19.2 | 90% equilibrium catalyst | 44.78 | 4.17 | 19.79 |
| E20.1 | 83% | 10% CEZ20.1 | 90% equilibrium catalyst | 36.30 | 3.83 | 18.70 |
| E20.2 | 91% | 10% CEZ20.2 | 90% equilibrium catalyst | 44.95 | 4.19 | 19.77 |
| E21.1 | 82% | 10% CEZ21.1 | 90% equilibrium catalyst | 33.67 | 3.68 | 16.88 |
| E21.2 | 83% | 10% CEZ21.2 | 90% equilibrium catalyst | 35.02 | 3.75 | 17.56 |
| E1 | 74% | 10% DCEZ1 | 90% equilibrium catalyst | 30.23 | 3.04 | 13.45 |
| E2 | 75% | 10% DCEZ2 | 90% equilibrium catalyst | 32.03 | 3.20 | 14.53 |
| E3 | 72% | 10% DCEZ3 | 90% equilibrium catalyst | 30.36 | 3.16 | 13.78 |
| E4 | 76% | 10% DCEZ4 | 90% equilibrium catalyst | 32.43 | 3.33 | 14.97 |
| E5 | 68% | 10% DCEZ5 | 90% equilibrium catalyst | 26.43 | 3.49 | 11.58 |
| E6 | 75% | 10% DCEZ6 | 90% equilibrium catalyst | 32.57 | 3.33 | 15.55 |
| E7 | 60% | 10% DCEZ7 | 90% equilibrium catalyst | 21.67 | 3.43 | 10.63 |
| E8 | 65% | 10% DCEZ8 | 90% equilibrium catalyst | 28.79 | 2.98 | 12.81 |

TABLE 4-continued

| Example/ Comparative Example | D value of Catalytic Cracking Auxiliary | Catalyst Mixture | | Material Balance, wt % | | |
|---|---|---|---|---|---|---|
| | | | | Liquefied Gas | Ethylene Yield | Propylene Yield |
| E9 | 75% | 10% DCEZ9 | 90% equilibrium catalyst | 31.44 | 3.10 | 13.99 |
| E10 | 73% | 10% DCEZ10 | 90% equilibrium catalyst | 33.31 | 3.26 | 15.11 |
| E11 | 76% | 10% DCEZ11 | 90% equilibrium catalyst | 31.57 | 3.22 | 14.33 |
| E12 | 73% | 10% DCEZ12 | 90% equilibrium catalyst | 33.73 | 3.40 | 15.57 |
| E13 | 65% | 10% DCEZ13 | 90% equilibrium catalyst | 27.49 | 3.56 | 12.04 |
| E14 | 73% | 10% DCEZ14 | 90% equilibrium catalyst | 33.87 | 3.40 | 16.17 |
| E15 | 63% | 10% DCEZ15 | 90% equilibrium catalyst | 22.54 | 3.50 | 11.06 |
| E16 | 64% | 10% DCEZ16 | 90% equilibrium catalyst | 29.94 | 3.04 | 13.32 |

The preferred embodiments of the present invention have been described in detail above, but the present invention is not limited to the specific details in the above embodiments. Within the scope of the technical concept of the present invention, various simple modifications can be made to the technical solutions of the present invention. These simple modifications all belong to the protection scope of the present invention.

In addition, it should be noted that each specific technical feature described in the above-mentioned embodiments may be combined in any suitable manner under the circumstance that there is no contradiction. In order to avoid unnecessary repetition, various possible combinations are not described in the Detailed Description of the Invention.

In addition, various combinations of different embodiments of the present invention can also be combined arbitrarily, as long as they do not violate the idea of the present invention, they should also be regarded as the disclosed contents of the present invention.

The invention claimed is:

1. A catalytic cracking agent, having an active component consisting of a phosphorus-modified molecular sieve and a non-phosphorus-modified molecular sieve or only consisting of a phosphorus-modified molecular sieve, characterized in that:
   (i) the active component consists of the phosphorus-modified molecular sieve and a non-phosphorus-modified molecular sieve,
      wherein the catalyst cracking agent has a D value of phosphorus in the catalytic cracking agent, determined with an electron probe microanalysis (EPMA), of ≥65%, and
      wherein said catalytic cracking agent contains, on the dry basis:
      1-25 wt % of a non-phosphorus-modified molecular sieve;
      5-50 wt % of a phosphorus-modified molecular sieve;
      1-60 wt % of an inorganic binder; and
      optionally, 0-60 wt % of a second clay; or
   (ii) the active component only consists of the phosphorus-modified molecular sieve,
      wherein the catalyst cracking agent has a D value of phosphorus in the catalytic cracking agent of ≥82%, and
      wherein, on the dry basis, said catalytic cracking agent contains:
      5-75 wt % of a phosphorus-modified molecular sieve;
      1-40 wt % of an inorganic binder; and
      optionally, 0-65 wt % of a second clay.

2. The catalytic cracking agent according to claim 1, wherein said phosphorus-modified molecular sieve is a phosphorus-modified MFI-structured molecular sieve, and said non-phosphorus-modified molecular sieve is a FAU-structured molecular sieve.

3. The catalytic cracking agent according to claim 1, wherein said catalytic cracking agent is a catalytic cracking catalyst, having an active component consisting of a phosphorus-modified MFI-structured molecular sieve and a non-phosphorus-modified FAU-structured molecular sieve; or
   wherein said catalytic cracking agent is a catalytic cracking auxiliary, having an active component consisting of a phosphorus-modified MFI-structured molecular sieve.

4. The catalytic cracking agent according to claim 1, wherein said non-phosphorus-modified molecular sieve is at least one of a PSRY molecular sieve, a rare earth-containing PSRY molecular sieve, an USY molecular sieve, a rare earth-containing USY molecular sieve, a REY molecular sieve, a REHY molecular sieve and an HY molecular sieve.

5. The catalytic cracking agent according to claim 1, wherein the inorganic binder comprises at least one compound selected from pseudo-boehmite, alumina sol, silica-alumina sol, water glass, and phosphorus-aluminum inorganic binder.

6. The catalytic cracking agent according to claim 5, wherein
the phosphorus-aluminum inorganic binder is a phosphorus aluminate binder and/or a first clay-containing phosphorus-aluminum inorganic binder.

7. The catalytic cracking agent according to claim 6, wherein
the first clay-containing phosphorus-aluminum inorganic binder is based on the dry basis, the first clay-containing phosphorus-aluminum inorganic binder contains 15-40 wt % of an aluminum component (as $Al_2O_3$), 45-80 wt % of a phosphorus component (as $P_2O_5$) and greater than 0 and not more than 40 wt % of a first clay, and the first clay-containing phosphorus-aluminum inorganic binder has a P/Al weight ratio of 1.0-6.0, a pH of 1-3.5, and a solid content of 15-60 wt %, wherein the first clay comprises at least one compound selected from kaolin, sepiolite, attapulgite, rectorite, montmorillonite, and diatomite.

8. The catalytic cracking agent according to claim 3, wherein
based on the total amount of said catalytic cracking catalyst, the inorganic binder comprises, on the dry basis, 3-39 wt % of a phosphorus-aluminum inorganic binder and 1-30 wt % of an inorganic binder selected from pseudo-boehmite, alumina sol, silica alumina sol, water glass, and mixtures thereof.

9. The catalytic cracking agent according to claim 1, wherein
the second clay comprises at least one compound selected from kaolin, sepiolite, attapulgite, rectorite, montmorillonite, glagerite, halloysite, hydrotalcite, bentonite, and diatomite.

10. A process for preparing the catalytic cracking agent according to claim 1, comprising:
(1) mixing a raw material and slurrying the raw material, and shaping into shaped bodies, wherein the raw material comprises:
a phosphorus-modified molecular sieve,
optionally, a non-phosphorus-modified molecular sieve,
an inorganic binder, and
optionally, a second clay; and
(2) carrying out a hydrothermal calcining treatment on the shaped bodies to obtain the catalytic cracking agent according to claim 1;
wherein
said phosphorus-modified molecular sieve is obtained by impregnating a molecular sieve having a temperature of 0-150° C. with an aqueous solution of a phosphorus-containing compound having a temperature of 0-150° C.; and
said hydrothermal calcining treatment is performed under a gauge pressure of 0.01-1.0 MPa at a temperature of 200-800° C. in an atmosphere of 100% water vapor or in an air atmosphere having a moisture content of at least 1%.

11. The process according to claim 10, wherein
said molecular sieve is a micropore ZSM-5 molecular sieve or a hierarchical ZSM-5 molecular sieve.

12. The process according to claim 10, wherein the molar ratio of phosphorus in the phosphorus-containing compound to aluminum in the molecular sieve is 0.01-2.

13. The process according to claim 10, wherein
the phosphorus-containing compound is selected from an organic phosphorus compound and/or an inorganic phosphorus compound;
wherein the organic phosphorus compound is selected from trimethyl phosphate, triphenylphosphine, trimethyl phosphite, tetrabutylphosphonium bromide, tetrabutylphosphonium chloride, tetrabutylphosphonium hydroxide, triphenylethylphosphonium bromide, triphenylbutylphosphonium bromide, triphenylbenzylphosphonium bromide, hexamethylphosphoric triamide, dibenzyl diethylphosphoramidite, and 1, 3-bis((triethylphosphaneyl)methyl)benzene; and
the inorganic phosphorus compound is selected from phosphoric acid, ammonium hydrogen phosphate, diammonium hydrogen phosphate, ammonium phosphate, and boron phosphate.

14. The process according to claim 10, wherein
in said molecular sieve, the content of $Na_2O$ is less than 0.1 wt %.

15. The process according to claim 10, wherein
the inorganic binder is a phosphorus-aluminum inorganic binder;
the phosphorus-aluminum inorganic binder is a first clay-containing phosphorus-aluminum inorganic binder; and
the first clay-containing phosphorus-aluminum inorganic binder is prepared with the following steps: an alumina source, a first clay and water are slurried to disperse into a slurry having a solid content of 5-48 wt %,
wherein said alumina source is aluminum hydroxide that can be peptized with an acid and/or alumina, relative to 15-40 parts by weight of the alumina source as $Al_2O_3$, and the amount of the first clay based on the dry weight is greater than 0 part by weight and not more than 40 parts by weight; and a concentrated phosphoric acid is added to the slurry under stirring according to the weight ratio of P/Al=1-6, and the resulting mixed slurry is reacted at 50-99° C. for 15-90 minutes, wherein P in the P/Al is the weight of phosphorus in the phosphoric acid, Al is the weight of aluminum in the alumina source.

16. The process according to claim 10, wherein said shaping is pelleting by spray-drying.

17. The process according to claim 10, wherein
said hydrothermal calcining treatment is carried out at a gauge pressure of 0.1-0.8 MPa in an atmosphere of 100% water vapor or an air atmosphere having a moisture content of at least 30% at 200-800° C.; and
said impregnating step is carried out with a weight ratio of water/molecular sieve of 0.5-1 at 50-150° C. for 0.5-40 hours.

18. A process for catalytically cracking a hydrocarbon oil, comprising
contacting the hydrocarbon oil with a mixture containing a catalytic cracking auxiliary and a catalytic cracking catalyst under a catalytic cracking condition,
wherein:
the catalytic cracking auxiliary is the catalytic cracking agent according to claim 1;
the content of the catalytic cracking auxiliary in said mixture is 0.1-30 wt %;
the catalytic cracking condition includes a reaction temperature of 500-800° C.; and
the hydrocarbon oil is one or more selected from crude oil, naphtha, gasoline, atmospheric residue, vacuum residue, atmospheric gas oil, vacuum gas oil, straight-run gas oil, propane light/heavy deasphalted oil, coker gas oil, and coal liquefication product.

19. A preparation system for preparing the catalytic cracking agent according to claim 1, comprising a phosphorus-modification device, a raw material mixing device, a shaping device, and a pressurized hydrothermal calcining device, and is configured to produce the catalytic cracking agent according to claim 1,
  wherein,
  the phosphorus-modification device comprises an equipment for introducing a solution of a phosphorus-containing compound; and/or
  the raw material mixing device receives raw materials, wherein the raw materials include:
  an impregnation-treated phosphorus-modified molecular sieve obtained from the phosphorus-modification device, a phosphorus-aluminum inorganic binder from a treatment device of phosphorus-aluminum inorganic binder, optionally a non-phosphorus-modified molecular sieve, and optionally a clay; and/or
  said shaping device is a device of shaping by spray-drying; and/or
  said pressurized hydrothermal calcining device is provided with an aqueous solution inlet and a gas pressurization joint.

* * * * *